US010195258B2

(12) United States Patent
Maeda et al.

(10) Patent No.: US 10,195,258 B2
(45) Date of Patent: *Feb. 5, 2019

(54) TAPE PREPARATION OF WT1 PEPTIDE CANCER VACCINE FOR TRANSDERMAL ADMINISTRATION

(71) Applicants: NITTO DENKO CORPORATION, Osaka (JP); OSAKA UNIVERSITY, Osaka (JP)

(72) Inventors: Yoshiki Maeda, Osaka (JP); Katsuyuki Okubo, Osaka (JP); Daisuke Asari, Osaka (JP); Arimichi Okazaki, Osaka (JP); Takuya Shishido, Osaka (JP); Mitsuhiko Hori, Osaka (JP); Haruo Sugiyama, Osaka (JP)

(73) Assignees: NITTO DENKO CORPORATION, Osaka (JP); OSAKA UNIVERSITY, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/166,954

(22) Filed: Jan. 29, 2014

(65) Prior Publication Data
US 2014/0220105 A1 Aug. 7, 2014

(30) Foreign Application Priority Data

Feb. 5, 2013 (JP) ................................. 2013-020798

(51) Int. Cl.
A61K 39/00 (2006.01)
A61K 9/70 (2006.01)
(52) U.S. Cl.
CPC ........ A61K 39/0011 (2013.01); A61K 9/7023 (2013.01); A61K 2039/54 (2013.01)
(58) Field of Classification Search
None
See application file for complete search history.

(56) References Cited

U.S. PATENT DOCUMENTS

| 7,030,212 | B1 | 4/2006 | Sugiyama et al. |
| 2004/0109869 | A1* | 6/2004 | Glenn ................... A61K 9/7061 424/185.1 |
| 2005/0215501 | A1* | 9/2005 | Lipford et al. ................. 514/44 |
| 2007/0082860 | A1 | 4/2007 | Sugiyama et al. |
| 2008/0112974 | A1 | 5/2008 | Czerkinsky et al. |
| 2008/0193487 | A1 | 8/2008 | Schild et al. |
| 2008/0286296 | A1 | 11/2008 | Ebensen et al. |
| 2010/0047327 | A1 | 2/2010 | Kuwahara et al. |
| 2010/0143400 | A1* | 6/2010 | Davis ................... A61K 39/145 424/197.11 |
| 2010/0189641 | A1* | 7/2010 | Chang ................. A61K 39/0011 424/1.11 |
| 2011/0070251 | A1* | 3/2011 | Sugiyama ................. 424/185.1 |
| 2012/0045465 | A1* | 2/2012 | Sugiyama ................. 424/185.1 |
| 2014/0220055 | A1 | 8/2014 | Okubo et al. |
| 2014/0220063 | A1 | 8/2014 | Asari et al. |
| 2014/0220100 | A1 | 8/2014 | Okubo et al. |
| 2015/0150975 | A1* | 6/2015 | Tanaka ................... A61K 47/12 424/185.1 |

FOREIGN PATENT DOCUMENTS

| EP | 2228072 A1 | 9/2010 |
| JP | 07-505883 A | 6/1995 |
| JP | 2002-531415 A | 9/2002 |
| JP | 2007-529531 A | 10/2007 |
| JP | 200874763 A | 4/2008 |
| JP | 2008127277 A * | 6/2008 |
| JP | 4422903 B2 | 12/2009 |
| JP | 2014169277 A | 9/2014 |
| JP | 2014169278 A | 9/2014 |
| JP | 2014169281 A | 9/2014 |
| RU | 2192884 C2 | 11/2002 |
| WO | 9320847 A1 | 10/1993 |
| WO | 2000006602 A1 | 2/2000 |
| WO | 00/32228 A2 | 6/2000 |
| WO | 2003106682 A1 | 12/2003 |
| WO | 2005/087238 A2 | 9/2005 |
| WO | 2008093772 A1 | 8/2008 |

OTHER PUBLICATIONS

Inoue et al. (Journal of Investigative Dermatology, 2007, 127:614-621).*
Karande et al. (Annual Rev. Chem. Biomol. Eng., 2010, 1:175-201).*
Lim et al.,Int. Immunopharmacol. Jan. 2003; 3(1): 115-118.*
Rechtsteiner et al. Journal of Immunology, 2005, 2476-2480.*
Yoshihiro Oka et al., Current Opinion in Immunology, vol. 20, pp. 211-220 (2008).
Hosoi Akihiro et al, Cancer Research, vol. 68, pp. 3941-3949 (2008).
Zhengrong Cui et al., Pharmaceutical Research, vol. 19, No. 7, pp. 947-953 (2002).
Extended European Search Report of EP 14000321 dated Apr. 7, 2014.
European Office Action issued with respect to European application No. 14000321.1, dated Dec. 15, 2016.
Japanese Office Action from Application No. 2014-014805 dated Oct. 31, 2017.

(Continued)

Primary Examiner — Daniel C Gamett
(74) Attorney, Agent, or Firm — Greenblum & Bernstein, P.L.C.

(57) ABSTRACT

The present invention provides a cancer vaccine tape preparation for inducing cellular immunity, comprising:
  a support,
  an adhesive layer comprising an adhesive disposed on one side of the support, wherein the adhesive layer carries a combination of:
  (i) a WT1 peptide and/or a modified WT1 peptide; and
  (ii) a first cellular immunity induction promoter. The tape preparation can provides high efficacy.

15 Claims, 3 Drawing Sheets
Specification includes a Sequence Listing.

(56) References Cited

OTHER PUBLICATIONS

Russian Office Action from Application No. 2014102937 dated Dec. 26, 2017.
Russian Search Report from Application No. 2014102937 dated Dec. 26, 2017.
European Office Action from Application No. 1400032.1 dated Jan. 9, 2018.
Chinese Office Action for Application No. 2014-10042748.8 dated Jun. 11, 2018.
Chinese Office Action from Patent Application No. 201410042748.8 dated Jul. 26, 2017.

\* cited by examiner

TAPE PREPARATION OF WT1 PEPTIDE CANCER VACCINE FOR TRANSDERMAL ADMINISTRATION

SEQUENCE LISTING

The instant application contains a Sequence Listing which has been submitted electronically in ASCII format and is hereby incorporated by reference in its entirety. Said ASCII copy, created on Mar. 24, 2014, is named P45218_SL.txt and is 2,636 bytes in size.

TECHNICAL FIELD

The present invention relates to a cancer vaccine tape preparation for transdermal administration comprising a WT1 peptide and/or a modified WT1 peptide, and a cellular immunity induction promoter.

BACKGROUND ART

There are a cancer vaccine that prevents virus infection to prevent a cancer caused by the virus, and a cancer vaccine which provides the result that cancer cells are specifically attacked by the immune system via the recognition of a cancer-specific antigen by the immune mechanism, particularly, the cellular immune mechanism in which cytotoxic T cells (CTL) play an important role. The former is not effective at all for a cancer in which the virus does not participate. The latter is a cancer therapeutic strategy of targeting an antigen possessed by a cancer cell itself. It is considered that the latter is widely effective for cancers having antigen by specifying the antigen. Inter alia, a cancer vaccine based on the viewpoint of the latter can treat tumors that are difficult to remove by surgical operation because of their size, and causes less side effects as compared with the conventional therapies such as chemotherapy and radiation therapy.

WT1 (Wilm's tumor 1) gene is overexpressed in many hematopoietic tumors and solid cancers, for example, acute myelocytic leukemia, acute lymphocytic leukemia, chronic myelocytic leukemia, myelodysplastic syndrome, multiple myeloma, non-Hodgkin's lymphoma, lung cancer, breast cancer, stomach cancer, large intestine/rectum cancer, pancreas cancer, bile duct cancer, head and neck squamous cell cancer, thyroid cancer, kidney cancer, prostate cancer, ovarian cancer, uterine cancer, bone soft tissue sarcoma, malignant melanoma, malignant mesothelioma, testicular germ cell tumor and malignant glioma. Those cancers overproduce the WT1 protein. The WT1 protein is fragmented in the cancer cell to produce partial peptides consisting of 8 to 12 amino acids. A WT1 peptide is one of the peptide fragment which has been bound with the MHC class I molecule in a cancer cell, moved to the surface of the cancer cell, and presented as an antigen bound to the MHC class I molecule on the cancer cell surface. The WT1 peptide becomes a mark of the cancer cell. The amino acid sequence of the WT1 peptide conforms to the type of the MHC class I molecule of the cell. For example, in the case of a cell having HLA-A*0201-type MHC, a HLA-A*0201-type MHC restricted WT1 peptide such as Db126 peptide consisting of 9 amino acids is generated, and in the case of a cell having HLA-A*2402-typeMHCa HLA-A*2402-type MHC restricted WT1 peptide such as Db235 peptide consisting of 9 amino acids is generated. In the case of a cell having other MHC, such as HLA-A26 type (WO 2005/095598), HLA-A*3303 type (WO 2007/097358), or HLA-A*1101 type (WO 2008/081701), each MHC restricted WT1 peptide is generated. When a WT1 peptide, or a modified WT1 peptide in which a part of amino acids of the WT1 peptide is substituted or modified is administered to a living body as an antigen (herein, a WT1 peptide or a modified WT1 peptide which has been administered as an antigen is referred to as "WT1 antigen peptide"), the WT1 antigen peptide is bound to the MHC Class I molecule on the surface of a dendritic cell which is an antigen presenting cell, or the WT1 antigen peptide is once taken into a dendritic cell, bound to the MHC class I molecule of the dendritic cell and then, is moved to the surface of the dendritic cell, thereby, is presented as an antigen bound to the MHC class I molecule on the surface of the dendritic cell. An activated dendritic cell having the WT1 antigen peptide/MHC class I molecule complex is moved to the regional lymph node, and activates a CD8-positive T lymphocyte which recognizes the WT1 antigen peptide/MHC class I molecule complex to differentiate and proliferate the cell into a cytotoxic T cell (CTL). CTL recognizes tumor cells having the complex of a WT1 peptide (derived from the endogenous WT1 protein) of the same amino acid sequence as the WT1 antigen peptide and the MHC class I molecule, or a tumor cell having a complex of a WT1 peptide (derived from the endogenous WT1 protein) of an amino acid sequence having cross immunoreactivity with the WT1 antigen peptide and the MHC class I molecule, and attacks the recognized tumor cells. Therefore, the aforementioned various MHC restricted WT1 peptides such as Db126 peptide and Db235 peptide, and modified WT1 peptides in which a part of amino acids of them are substituted or modified are useful as cancer vaccines (Non-Patent Document 1).

It is also known that an adjuvant is utilized in order to enhance the action as cancer vaccine of the WT1 peptide and/or the modified WT1 peptide. As the adjuvant for the WT1 peptide and/or the modified WT1 peptide, for example, mineral gels such as aluminum hydroxide; surfactants such as lysolecithin, and pluronicpolyol; polyanions; peptides; or oil emulsions (Patent Document 1), and GM-CSF, BCG-CWS and Montanide ISA51 (Non-Patent Document 1) are known. In addition to them, a variety of vaccine adjuvants including cyclic dinucleotide analogs (Patent Document 3 and Patent Document 4) such as 1H-imidazo[4,5-c] quinoline-4-amine, imiquimod (Patent Document 2), and cyclic di-GMP (c-di-GMP), and TLR2, 3, 7, 8 and 9 ligands (Patent Document 5) have been known. In addition, it is also known that immunity induced by transdermal administration of imiquimod-containing peptide is further enhanced by adding Peptide-25 (Non-Patent Document 2).

In general, vaccines are administered by subcutaneous or intradermal injection. In addition to those routes, immunity induction by a variety of administration routes, for example, transdermal administration (Patent Document 5 and Non-Patent Document 2), and mucosal administration such as, buccal administration, nasal administration, and sublingual administration (Non-Patent Document 3, Patent Document 6, and Patent Document 7) have been tried.

LIST OF DOCUMENTS

[Patent Document 1] Japanese Patent No. 4422903
[Patent Document 2] JP 7-505883 A
[Patent Document 3] JP 2007-529531 A
[Patent Document 4] US Patent Application Publication No. 2008/0286296
[Patent Document 5] US Patent Application Publication No. 2008/0193487

[Patent Document 6] JP 2002-531415 A
[Patent Document 7] US Patent Application Publication No. 2008/0112974
[Non-Patent Document 1] Yoshihiro Oka et al., Current Opinion in Immunology, 20: 211-220 (2008)
[Non-Patent Document 2] Hosoi Akihiro et al., Cancer Research, 68, 3941-3949 (2008)
[Non-Patent Document 3] Zhengrong Cui et al., Pharmaceutical Research, Vol. 19, No. 7, 947-953 (2002)

SUMMARY OF THE INVENTION

It is well-known that an adjuvant is used to enhance efficacy of a vaccine. Suitable adjuvants generally vary depending on, for example, the kind of the antigen, the administration route, and the immune response which is desired to be induced (i.e. cellular immunity or humoral immunity). Further, in addition to the adjuvant, there are a variety of substances which promote the induction of the immunity. Then, an object of the present invention is to provide a tape preparation for transdermal administration of a cancer vaccine composition with higher efficacy and is convenient for use.

A microorganism or a virus itself, or a part of them is contained in a widely used vaccine and the vaccine is administered to induce immune response. Usually, since invasion of the microorganism or virus is inhibited by the skin due to the size thereof, it is necessary that the vaccine is invasively administered into the body. Therefore, vaccines are usually administered by injection. However, the injection has some problems including pain, fear, injection scar, and subsequent scarring cicatrization. People other than health care workers are not permitted to perform the injection. Intradermal injection which can introduce higher immune response is a difficult administration technique. There is a risk of accidental infection of the health care workers due to needlestick injury. Patients are needed to visit the hospital repeatedly when administration is performed repetitively. Medical wastes which necessitate special disposition such as injection needles are generated. In view of the above issues, injection is not necessarily the optimal administration route.

It seems that cream formulations for transdermal administration or mucosal administration may solve the various problems described above with regard to injection. However, cream formulations have some disadvantages, for example, the drug amount to be administered is apt to vary widely and unstably, or the fingers used for application get dirty. In particular, when the eyes are rubbed with a dirtied finger, there is a possibility that the drug may get into the eyes and cause irritation.

A WT1 peptide and/or a modified WT1 peptide can activate CTL (cytotoxic T cell) via a MHC class I molecule, that is, the peptide can induce cellular immunity. The WT1 peptide and/or the modified WT1 peptide are a molecule having a molecular weight of about 700 to about 1600 and consisting of 8 to 12 amino acids, and are significantly smaller than microorganisms or virus itself although they are not considered as a small-molecule substance. It may be possible that they are administered by a route other than injection. However, a preparation for the administration of the peptide vaccine in a rout other than injection has not been developed yet. The reason includes many things, for example: a suitable substance that can promote to induce the cellular immunity has been unknown; it has also been unknown whether or not an antigen can be delivered to a tissue suitable for the induction of the cellular immunity.

Inter alia, a substance that can promote to induce the cellular immunity when it is used with the antigen when administered in a route other than injection has been unknown.

The inventors have found that the cellular immunity can effectively be induced by transdermal administration of the peptide vaccine. The inventors have also found some substances suitable for enhancing cellular immunity induced by the transdermal administration of a WT1 peptide and/or a modified WT1 peptide. The substances may include TLR ligands such as a TLR1/2 ligand, a TLR2 and Dectin1 ligand, a TLR2/6 ligand, a TLR3 ligand, a TLR4 ligand, a TLR5 ligand, a TLR7 and/or TLR8 ligand, and a TLR9 ligand; cyclic dinucleotides such as cyclic di-GMP and cyclic di-AMP; immunomodulatory small molecule drugs such as bestatin, pidotimod and levamisole hydrochloride; cyclooxygenase inhibitors such as etodolac and loxoprofen; prostaglandin receptor antagonists such as an EP2 receptor antagonist, an EP4 receptor antagonist, a DP receptor antagonist, and an IP receptor antagonist; prostaglandin receptor agonists such as an EP3 receptor agonist; TSLP production inhibitors such as berberine chloride and naringenin; adenylate cyclase inhibitors such as 2′,5′-dideoxyadenosine and niacin; omega-3 fatty acids such as eicosapentaenoic acid and docosahexaenoic acid; PPAR agonists such as a PPAR-aagonist, a PPAR-δ agonist, and a PPAR-γ agonist; dopamine receptor antagonists such as a D1 receptor antagonist, and a D5 receptor antagonist; dopamine receptor agonists such as a D2 receptor agonist, a D3 receptor agonist, and a D4 receptor agonist; histamine receptor antagonists such as a H1 receptor antagonist, and a H2 receptor antagonist; histamine receptor agonists such as a H1 receptor agonist, a H3 receptor agonist, and a H4 receptor agonist; serotonin receptor antagonists such as a 5-HT2 receptor antagonist, a 5-HT4 receptor antagonist, a 5-HT6 receptor antagonist, and a 5-HT7 receptor antagonist; serotonin receptor agonists such as a 5-HT1 receptor agonist, and a 5-HT2 receptor agonist; vasopressin receptor antagonists such as a V2 receptor antagonist; vasopressin receptor agonists such as a V1 receptor agonist; muscarine receptor antagonists such as a M1 receptor antagonist, a M3 receptor antagonist, and a M5 receptor antagonist; muscarine receptor agonists such as a M1 receptor agonist, a M2 receptor agonist, a M3 receptor agonist, a M4 receptor agonist, and a M5 receptor agonist; adrenalin receptor antagonists such as an α1 receptor antagonist, a β1 receptor antagonist, a β2 receptor antagonist, and a β3 receptor antagonist; adrenalin receptor agonists such as an α1 receptor agonist, and an α2 receptor agonist; angiotensin receptor agonists such as an AT2 receptor agonist; GABA receptor agonists such as a $GABA_B$ receptor agonist; thrombin receptor antagonists such as a PAR-1 receptor antagonist; thrombin receptor agonists such as a PAR-1 receptor agonist; opioid receptor agonists such as buprenorphine; leukotriene receptor antagonists such as a CysLT1 receptor antagonist, and a CysLT2 receptor antagonist; leukotriene receptor agonists such as a BLT receptor agonist; ADP receptor agonists such as adenosine diphosphate; melatonin receptor agonists such as melatonin; somatostatin receptor agonists such as octreotide; cannabinoid receptor agonists such as dronabinol; sphingosine-1 phosphate receptor agonists such as fingolimod; metabotropic glutamate receptor agonists such as an mGluR2 receptor agonist, an mGluR3 receptor agonist, an mGluR4 receptor agonist, an mGluR6 receptor agonist, an mGluR7 receptor agonist, and an mGluR8 receptor agonist; phospholipase A2 inhibitors such as glycyrrhizic acid; TGF-β production inhibitors such as pirfenidone; Th2 cytokine inhibitors such as suplatast tosylate; and pharmacologically acceptable acids such as decanoic acid, lauric acid, myristic acid, isostearic acid and oleic acid, or salts thereof. Further, the inventors have found that a helper peptide such as Peptide-25 or hWT1$_{35}$ is also useful to promote the induction of the cellular immunity induced by transdermal administration of a WT1 peptide and/or a modified WT1 peptide, when it is used in place of or in addition to the above-discussed substances. That is, it is found that cellular immunity is remarkably enhanced by a combination of a TLR ligand and a helper peptide, a combination of a cyclic dinucleotide and a helper peptide, a combination of an immunomodulatory small molecule drug and a helper peptide, a combination of a cyclooxygenase inhibitor and a helper peptide, a combination of a prostaglandin receptor antagonist and a helper peptide, a combination of a prostaglandin receptor agonist and a helper peptide, a combination of a TSLP production inhibitor and a helper peptide, a combination of an adenylate cyclase inhibitor and a helper peptide, a combination of an omega-3 fatty acid and a helper peptide, a combination of a PPAR agonist and a helper peptide, a combination of a dopamine receptor antagonist and a helper peptide, a combination of a dopamine receptor agonist and a helper peptide, a combination of a histamine receptor agonist and a helper peptide, a combination of a histamine receptor antagonist and a helper peptide, a combination of a serotonin receptor agonist and a helper peptide, a combination of a serotonin receptor antagonist and a helper peptide, a combination of a vasopressin receptor antagonist and a helper peptide, a combination of a vasopressin receptor agonist and a helper peptide, a combination of a muscarine receptor antagonist and a helper peptide, a combination of a muscarine receptor agonist and a helper peptide, a combination of an adrenalin receptor antagonist and a helper peptide, a combination of an adrenalin receptor agonist and a helper peptide, a combination of an angiotensin receptor agonist and a helper peptide, a combination of a GABA receptor agonist and a helper peptide, a combination of a thrombin receptor antagonist and a helper peptide, a combination of a thrombin receptor agonist and a helper peptide, a combination of an opioid receptor agonist and a helper peptide, a combination of an ADP receptor agonist and a helper peptide, a combination of a leukotriene receptor antagonist and a helper peptide, a combination of a leukotriene receptor agonist and a helper peptide, a combination of a melatonin receptor agonist and a helper peptide, a combination of a somatostatin receptor agonist and a helper peptide, a combination of a cannabinoid receptor agonist and a helper peptide, a combination of a sphingosine-1 phosphate receptor agonist and a helper peptide, a combination of a metabotropic glutamate receptor agonist and a helper peptide, a combination of a phospholipase A2 inhibitor and a helper peptide, a combination of a TGF-β production inhibitor and a helper peptide, or a combination of a Th2 cytokine inhibitor and a helper peptide. In a particularly preferred aspect, cellular immunity is remarkably enhanced by a combination of a TLR ligand and a helper peptide, or a combination of a cyclic dinucleotide and a helper peptide, or a combination of a pharmacologically acceptable acid or a pharmacologically acceptable salt thereof and a helper peptide. It was also found that the adhesive is preferably an acrylic adhesive, a rubber-based adhesive (PIB-based, SIS-based or PIB/SIS mixture-based adhesive), or a silicone-based adhesive, and the adhesive layer may further contain a fatty acid ester such as isopropyl myristate (IPM) or isopropyl palmitate (IPP), as an absorption accelerator. Further, it has been found that the high cellular immunity inducing effect is obtained by an administration under a mildly irritating condition. Specifically, the high cellular immunity inducing effect is obtained by selecting the mildly irritating state where transepidermal water loss (TEWL) (g/h·m$^2$), which is an index of the state of the skin of a model animal for skin irritation evaluation, before the administration of the cancer vaccine tape preparation is 50 or less, and applying the cancer vaccine tape preparation to the skin. Alternatively, a higher cellular immunity inducing effect can be obtained when the cancer vaccine tape preparation has such a mildly irritating property that the cutaneous TSLP level (pg/mg protein) of the model animal for skin irritation evaluation at the completion of the administration becomes 10000 or less.

Therefore, the present invention, in a first aspect, provides the aspects listed below:

(1) A cancer vaccine tape preparation for inducing cellular immunity in a subject, comprising:

a support, and an adhesive layer comprising an adhesive disposed on one side of the support, wherein the adhesive layer carries a combination of:

(i) a WT1 peptide and/or a modified WT1 peptide; and (ii) a first cellular immunity induction promoter selected from a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenaline receptor antagonist, an adrenaline receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, a Th2 cytokine inhibitor, and combinations of two or more kinds thereof wherein the tape preparation is applied to the skin of a subject;

(2) The cancer vaccine tape preparation according to (1), wherein the adhesive layer further carries a second cellular immunity induction promoter that is a pharmacologically acceptable acid or a pharmacologically acceptable salt thereof;

(3) The cancer vaccine tape preparation according to (1) or (2), wherein the first cellular immunity induction promoter is a TLR ligand;

(4) The cancer vaccine tape preparation according to (1) or (2), wherein the first cellular immunity induction promoter is a cyclic dinucleotide;

(5) The cancer vaccine tape preparation according to (1) or (2), wherein the first cellular immunity induction promoter is an immunomodulatory small molecule drug;

(6) The cancer vaccine tape preparation according to (1) or (2), wherein the first cellular immunity induction promoter is a cyclooxygenase inhibitor;

(7) The cancer vaccine tape preparation according to (1) or (2), wherein the first cellular immunity induction promoter is a prostaglandin receptor antagonist, and the prostaglandin receptor antagonist is an EP2 receptor antagonist, an EP4 receptor antagonist, a DP receptor antagonist or an IP receptor antagonist;

(8) The cancer vaccine tape preparation according to (1) or (2), wherein the first cellular immunity induction promoter is a prostaglandin receptor agonist, and the prostaglandin receptor agonist is an EP3 receptor agonist;

(9) The cancer vaccine tape preparation according to (1) or (2), wherein the first cellular immunity induction promoter is a TSLP production inhibitor;

(10) The cancer vaccine tape preparation according to (1) or (2), wherein the first cellular immunity induction promoter is an adenylate cyclase inhibitor;

(11) The cancer vaccine tape preparation according to (1) or (2), wherein the first cellular immunity induction promoter is an omega-3 fatty acid;

(12) The cancer vaccine tape preparation according to (1) or (2), wherein the first cellular immunity induction promoter is a PPAR agonist, and the PPAR agonist is a PPAR-α agonist, a PPAR-δ agonist, or a PPAR-γ agonist;

(13) The cancer vaccine tape preparation according to (1) or (2), wherein the first cellular immunity induction promoter is a dopamine receptor antagonist, and the dopamine receptor antagonist is a D1 receptor antagonist or a D5 receptor antagonist;

(14) The cancer vaccine tape preparation according to (1) or (2), wherein the first cellular immunity induction promoter is a dopamine receptor agonist, and the dopamine receptor agonist is a D2 receptor agonist, a D3 receptor agonist, or a D4 receptor agonist;

(15) The cancer vaccine tape preparation according to (1) or (2), wherein the first cellular immunity induction promoter is a histamine receptor antagonist, and the histamine receptor antagonist is a H1 receptor antagonist or a H2 receptor antagonist;

(16) The cancer vaccine tape preparation according to (1) or (2), wherein the first cellular immunity induction promoter is a histamine receptor agonist, and the histamine receptor agonist is a H1 receptor agonist, a H3 receptor agonist or a H4 receptor agonist;

(17) The cancer vaccine tape preparation according to (1) or (2), wherein the first cellular immunity induction promoter is a serotonin receptor antagonist, and the serotonin receptor antagonist is a 5-HT2 receptor antagonist, a 5-HT4 receptor antagonist, a 5-HT6 receptor antagonist, or a 5-HT7 receptor antagonist;

(18) The cancer vaccine tape preparation according to (1) or (2), wherein the first cellular immunity induction promoter is a serotonin receptor agonist, and the serotonin receptor agonist is a 5-HT1 receptor agonist or a 5-HT2 receptor agonist;

(19) The cancer vaccine tape preparation according to (1) or (2), wherein the first cellular immunity induction promoter is a vasopressin receptor antagonist, and the vasopressin receptor antagonist is a V2 receptor antagonist;

(20) The cancer vaccine tape preparation according to (1) or (2), wherein the first cellular immunity induction promoter is a vasopressin receptor agonist, and the vasopressin receptor agonist is a V1 receptor agonist;

(21) The cancer vaccine tape preparation according to (1) or (2), wherein the first cellular immunity induction promoter is a muscarine receptor antagonist, and the muscarine receptor antagonist is a M1 receptor antagonist, a M3 receptor antagonist, or a M5 receptor antagonist;

(22) The cancer vaccine tape preparation according to (1) or (2), wherein the first cellular immunity induction promoter is a muscarine receptor agonist, and the muscarine receptor agonist is a M1 receptor agonist, a M2 receptor agonist, a M3 receptor agonist, a M4 receptor agonist, or a M5 receptor agonist;

(23) The cancer vaccine tape preparation according to (1) or (2), wherein the first cellular immunity induction promoter is an adrenaline receptor antagonist, and the adrenaline receptor antagonist is an α1 receptor antagonist, a β1 receptor antagonist, a β2 receptor antagonist, or a β3 receptor antagonist;

(24) The cancer vaccine tape preparation according to (1) or (2), wherein the first cellular immunity induction promoter is an adrenaline receptor agonist, and the adrenaline receptor agonist is an α1 receptor agonist or an α2 receptor agonist;

(25) The cancer vaccine tape preparation according to (1) or (2), wherein the first cellular immunity induction promoter is an angiotensin receptor agonist, and the angiotensin receptor agonist is an AT2 receptor agonist;

(26) The cancer vaccine tape preparation according to (1) or (2), wherein the first cellular immunity induction promoter is a GABA receptor agonist, and the GABA receptor agonist is a $GABA_b$ receptor agonist;

(27) The cancer vaccine tape preparation according to (1) or (2), wherein the first cellular immunity induction promoter is a thrombin receptor antagonist, and the thrombin receptor antagonist is a PAR-1 receptor antagonist;

(28) The cancer vaccine tape preparation according to (1) or (2), wherein the first cellular immunity induction promoter is a thrombin receptor agonist, and the thrombin receptor agonist is a PAR-1 receptor agonist;

(29) The cancer vaccine tape preparation according to (1) or (2), wherein the first cellular immunity induction promoter is an opioid receptor agonist;

(30) The cancer vaccine tape preparation according to (1) or (2), wherein the first cellular immunity induction promoter is a leukotriene receptor antagonist, and the leukotriene receptor antagonist is a CysLT1 receptor antagonist or a CysLT2 receptor antagonist;

(31) The cancer vaccine tape preparation according to (1) or (2), wherein the first cellular immunity induction promoter is a leukotriene receptor agonist, and the leukotriene receptor agonist is a BLT receptor agonist;

(32) The cancer vaccine tape preparation according to (1) or (2), wherein the first cellular immunity induction promoter is a melatonin receptor agonist;

(33) The cancer vaccine tape preparation according to (1) or (2), wherein the first cellular immunity induction promoter is a somatostatin receptor agonist;

(34) The cancer vaccine tape preparation according to (1) or (2), wherein the first cellular immunity induction promoter is a cannabinoid receptor agonist;

(35) The cancer vaccine tape preparation according to (1) or (2), wherein the first cellular immunity induction promoter is a sphingosine-1 phosphate receptor agonist;

(36) The cancer vaccine tape preparation according to (1) or (2), wherein the first cellular immunity induction promoter is a metabotropic glutamate receptor agonist, and the metabotropic glutamate receptor agonist is a mGluR2 receptor agonist, a mGluR3 receptor agonist, a mGluR4 receptor agonist, a mGluR6 receptor agonist, a mGluR7 receptor agonist, or a mGluR8 receptor agonist;

(37) The cancer vaccine tape preparation according to (1) or (2), wherein the first cellular immunity induction promoter is an ADP receptor agonist;

(38) The cancer vaccine tape preparation according to (1) or (2), wherein the first cellular immunity induction promoter is a phospholipase A2 inhibitor;

(39) The cancer vaccine tape preparation according to (1) or (2), wherein the first cellular immunity induction promoter is a TGF-β production inhibitor;

(40) The cancer vaccine tape preparation according to (1) or (2), wherein the first cellular immunity induction promoter is a Th2 cytokine inhibitor;

(41) The cancer vaccine tape preparation of any one of (3) to (40), wherein the first cellular immunity induction promoter is a helper peptide;

(42) The cancer vaccine tape preparation according to (1) or (2), wherein the first cellular immunity induction promoter is a combination of a helper peptide and at least one substance selected from the group consisting of a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenaline receptor antagonist, an adrenaline receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor and a Th2 cytokine inhibitor;

(43) The cancer vaccine tape preparation according to any one of (1) to (42), wherein the adhesive is an acrylic adhesive;

(44) The cancer vaccine tape preparation according to any one of (1) to (42), wherein the adhesive is a rubber-based adhesive;

(45) The cancer vaccine tape preparation according to any one of (1) to (42), wherein the adhesive is a silicone-based adhesive;

(46) the cancer vaccine tape preparation according to any one of (43) to (45), wherein the adhesive layer further carries a skin permeability enhancer;

(47) The cancer vaccine tape preparation according to any one of (1) to (46), wherein the tape preparation is applied under a mildly irritating conditions;

(48) The cancer vaccine tape preparation according to (47), wherein the mildly irritating condition is a condition under which transepidermal water loss (TEWL) in a model animal for skin irritation evaluation before the application of the tape preparation is 50 g/h·m² or less; and

(49) The cancer vaccine tape preparation according to (47) or (48), wherein the mildly irritating condition is a condition under which the cutaneous TSLP level in a model animal for skin irritation evaluation at completion of the application of the tape preparation is 10000 pg/mg protein or less.

The present invention also provides the following embodiments:

(50) A method for inducing cellular immunity in a subject, which comprises applying a cancer vaccine tape preparation, comprising:

a support,
an adhesive layer comprising an adhesive disposed on one side of the support, wherein the adhesive layer carries a combination of:
(i) a WT1 peptide and/or a modified WT1 peptide; and
(ii) a first cellular immunity induction promoter selected from a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenaline receptor antagonist, an adrenaline receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, a Th2 cytokine inhibitor, and combinations of two or more kinds thereof to the skin of the subject;

(51) A method for treating or preventing a cancer in a subject, which comprises applying a cancer vaccine tape preparation, comprising:

a support,
an adhesive layer comprising an adhesive disposed on one side of the support, wherein the adhesive layer carries an effective amount of a combination of:
(i) a WT1 peptide and/or a modified WT1 peptide; and
(ii) a first cellular immunity induction promoter selected from a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenaline receptor antagonist, an adrenaline receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, a Th2 cytokine inhibitor, and combinations of two or more kinds thereof to the skin of the subject;

(52) A method of treating or preventing a cancer, comprising applying the cancer vaccine tape preparation according to any one of (1) to (49);

(53) A combination of (i) WT1 peptide and/or modified WT1 peptide and (ii) a first cellular immunity induction promoter selected from TLR ligand, cyclic dinucleotide, helper peptide, immunomodulatory small molecule drug, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor, Th2 cytokine inhibitor and a combination of two or more kids of them, for use in inducing cellular immunity by transdermal administration of WT1 peptide and/or modified WT1 peptide for use to induce cellular immunity in a subject, wherein the combination is formulated in a tape preparation comprising a support and an adhesive layer disposed on one side of the support comprising an adhesive and carrying the combination, and the tape preparation is applied to the skin of the subject;

(54) A combination of (i) WT1 peptide and/or modified WT1 peptide and (ii) a first cellular immunity induction promoter selected from TLR ligand, cyclic dinucleotide, helper peptide, immunomodulatory small molecule drug, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor, Th2 cytokine inhibitor and a combination of two or more kids of them, for use in the treatment or prevention of a cancer, wherein the combination is formulated in a tape preparation comprising a support and an adhesive layer disposed on one side of the support comprising an adhesive and carrying the combination; and

(55) Use of (i) WT1 peptide and/or modified WT1 peptide and (ii) a first cellular immunity induction promoter selected from TLR ligand, cyclic dinucleotide, helper peptide, immunomodulatory small molecule drug, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor, Th2 cytokine inhibitor and a combination of two or more kids of them for the manufacture of a cancer vaccine tape preparation for inducing cellular immunity in a subject.

Since the cancer vaccine tape preparation of the present invention is applied to the skin, it has the following advantages: excellent compliance, for example, non-invasive administration, no pain, and release from fear of injection; patients can administer the cancer vaccine tape preparation by himself/herself since the administration is simple; a risk of accidental infection due to needlestick injury by health care workers can be avoided; in the case of repetitive administration, the ambulatory frequency can be reduced, and this can contribute to the improvement in quality of life of the patient; and medical wastes which necessitate special disposition such as an injection needle are not generated. In addition, in the case of the tape preparation, unlike in the case of cream formulations, a predetermined dose can be surely administered, the drug releasing rate can be arbitrarily controlled, the cancer vaccine tape preparation is not adhered to other site upon administration, and it is possible to be detached. Further, since the tape preparation can be easily detached, in the case where a side effect is generated, the patient himself/herself can instantaneously stop the administration by removing the tape preparation from the application site. Further, there is also an advantage that efficacy of the cancer vaccine tape preparation of the present invention is remarkably improved, as compared with administration of the WT1 peptide and/or the modified WT1 peptide alone. Further, the cancer vaccine tape preparation of the present invention also has an advantage that transdermal administration of the tape preparation induces stronger cellular immunity as compared with injection administration of an antigen.

DETAILED DESCRIPTION OF THE INVENTION

Figure 1:
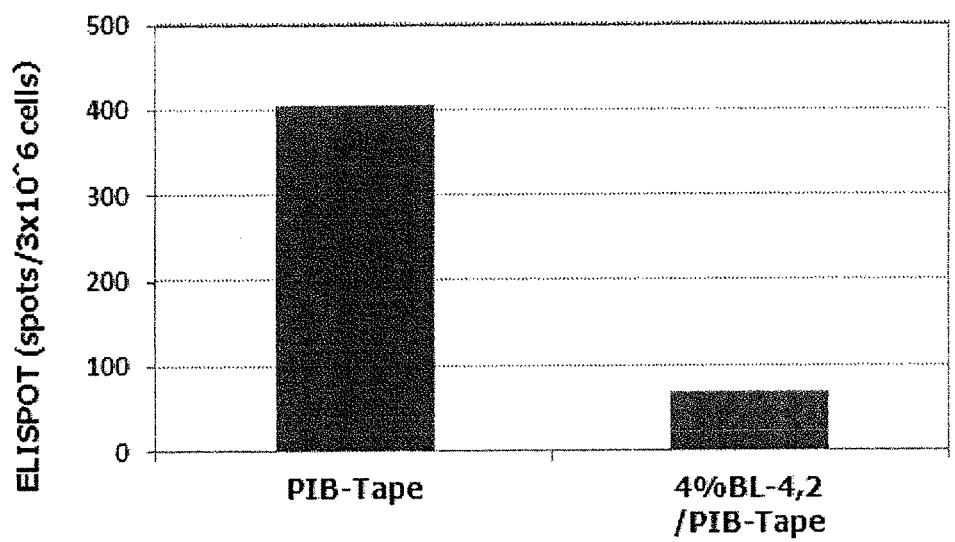
FIG. 1 is a diagram illustrating a comparison of immunity induction between a tape preparation containing no surfactant and a tape preparation containing a surfactant.

First, terms used in the present specification will be defined so that the present invention can be more easily understood. Terms having no definition have the meaning which is normally understood by a person skilled in the art in the fields of, particularly, medicine, pharmacy, immunology, cell biology, biochemistry, polymer chemistry and the like, unless the context requires otherwise.

I. Definition

As used herein, the term "WT1 peptide" means a partial peptide consisting of about 8 to about 15, preferably about 8 to about 12 amino acids. WT1 peptide is a peptide obtained by fragmenting the WT1 protein which is a product of cancer gene WT1 (Wilm's tumor), and includes Db126 peptide, Db235 antigen peptide and the like. In addition, a partial peptide of WT1 product disclosed in WO 2000/06602, a WT1-derived HLA-A26 binding cancer antigen peptide described in WO 2005/095598, a HLA-A*3303-restricted WT1 peptide described in WO 2007/097358, and a HLA-A*1101-restricted WT1 peptide described in WO 2008/081701 are also included in the "WT1 peptide" of the present invention.

The term "Db126 peptide" means a WT1 peptide consisting of a sequence Arg Met Phe Pro Asn Ala Pro Tyr Leu (SEQ ID No.: 1). The term "Db235 peptide" means a WT1 peptide consisting of a sequence Cys Met Thr Trp Asn Gln Met Asn Leu (SEQ ID No.: 2) (Patent Document 1).

As used herein, the term "modified WT1 peptide" means a peptide in which all or a part of amino acids of a WT1 peptide are modified by substitution, modification or the like.

The modified WT1 peptide includes, for example,
(a) a peptide consisting of an amino acid sequence in which one to several, for example, 1, 2, 3, 4 or 5 amino acids are substituted, deleted or added in an amino acid sequence of a WT1 peptide; and
(b) a peptide consisting of an amino acid sequence in which all or a part of amino acids, for example, one or more, for example, 1, 2, 3, 4, 5, 6, 7, 8, 9, 10, 11 or 12 amino acids are modified in an amino acid sequence of a WT1 peptide.

Examples of "modification" of an amino acid which can be possessed by a modified WT1 peptide include, but not limited to, aliphatic chain addition modification such as alkylation such as acetylation and methylation, glycosylation, hydroxylation, carboxylation, aldehydization, phosphorylation, sulfonylation, formylation, myristoylation, palmitoylation and stearoylation, octanoylation, esterification, amidation, deamidation, disulfide bond formation modification such as cystine modification, glutathione modification and thioglycolic acid modification, glycation, ubiquitination, succinimide formation, glutamylation, prenylation and the like. The modified WT1 peptide may contain a combination of substitution, deletion or addition of one or more amino acids, and modification of one or more amino acids.

As a specific example, Db235m peptide in which a part of Db235 peptide is modified is a modified WT1 peptide consisting of a sequence Cys Tyr Thr Trp Asn Gln Met Asn Leu (SEQ ID No.: 3) (WO 2002/079253), and is included in the modified WT1 peptide in the present invention. A WT1 substitution type peptide described in WO 2004/026897, a WT1$_{235-243}$ peptide derivative disclosed in WO 2007/063903 A1, and a HLA-A24 restricted cancer antigen peptide disclosed in WO 2003/106682 are also included in the modified WT1 peptide in the present invention.

The WT1 peptide and/or the modified WT1 peptide can be in the free form, or any pharmacologically acceptable salt form, for example, a form of acid salts (acetic acid salt, TFA salt, hydrochloric acid salt, sulfuric acid salt, phosphoric acid salt, lactic acid salt, tartaric acid salt, maleic acid salt, fumaric acid salt, oxalic acid salt, hydrobromic acid salt, succinic acid salt, nitric acid salt, malic acid salt, citric acid salt, oleic acid salt, palmitic acid salt, propionic acid salt, formic acid salt, benzoic acid salt, picric acid salt, benzenesulfonic acid salt, dodecylsulfuric acid salt, methanesulfonic acid salt, p-toluenesulfonic acid salt, glutaric acid salt, a variety of amino acid salts etc.), metal salts (alkali metal salts (e.g. sodium salt, potassium salt), alkaline earth metal salts (e.g. calcium salt, magnesium salt), aluminum salt etc.), or amine salts (triethylamine salt, benzylamine salt, diethanolamine salt, t-butylamine salt, dicyclohexylamine salt, arginine salt, dimethylammonium salt, ammonium salt etc.). A preferable pharmacologically acceptable salt is an acetic acid salt or a TFA salt. The WT1 peptide and/or the modified WT1 peptide which has been synthesized or produced, isolated and purified by a well-known method can be used.

As used herein, the term "cellular immunity induction promoter" means any substance which can enhance the cellular immune response induced by an antigen which is administered together with the substance, as compared with the immune response induced by the antigen without the substance. The cellular immunity induction promoter may include substances specified in the present specification, though it is not limited by the action mechanism by which induction of the cellular immunity is promoted.

As used herein, the term "TLR ligand" means a ligand of a Toll-like receptor (TLR), and includes, for example, ligands of TLR1 to 9. Examples of the TLR ligand include a TLR1/2 ligand, a TLR2/6 ligand, a TLR2 and Dectin1 ligand, a TLR3 ligand, a TLR4 ligand, a TLR5 ligand, a TLR7 and/or TLR8 ligand, a TLR9 ligand and the like. In a preferable aspect of the present invention, the TLR ligand is a TLR1/2 ligand, a TLR2 and Dectin1 ligand, a TLR3 ligand, a TLR4 ligand, a TLR7 and/or TLR8 ligand, and/or a TLR9 ligand.

As used herein, the term "TLR1/2 ligand" means a ligand of a heterodimer of a Toll-like receptor (TLR) 1 and a Toll-like receptor (TLR) 2, and includes, for example, a triacylated lipoprotein derived from a cell wall of a bacterium and a salt thereof, and these may be an extract, a product or a synthetic product, and are not limited to them.

In a preferable aspect of the present invention, the TLR1/2 ligand is Pam$_3$CSK$_4$. Pam$_3$CSK$_4$ has the formula ("Ser-Lys-Lys-Lys-Lys" disclosed as SEQ ID NO: 9):

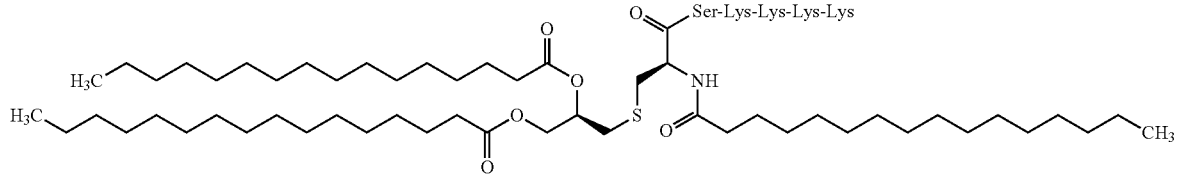

As used herein, the term "TLR2 and Dectin1 ligand" means a ligand of a Toll-like receptor (TLR) 2 and a β1,3-glucan receptor (Dectin1), and includes, for example, a β1,3-glucan derived from a cell wall of a fungus and a salt thereof, and these may be an extract, a product or a synthetic product, and are not limited to them. In a preferable aspect of the present invention, the TLR2 and Dectin1 ligand is Zymosan derived from a yeast cell wall.

As used herein, the term "TLR3 ligand" means a ligand of a Toll-like receptor (TLR) 3, and includes, for example, a double-stranded RNA (dsRNA) derived from a virus and a salt thereof, and these may be an extract, a product or a synthetic product, and are not limited to them. In a preferable aspect of the present invention, the TLR3 ligand is polyinosinic-polycytidylic acid (Poly(I:C)) which is a synthetic product and/or a salt thereof.

As used herein, the term "TLR4 ligand" means a ligand of a Toll-like receptor (TLR) 4, and includes, for example, a lipopolysaccharide (LPS) derived from a bacterium or a plant, particularly, a lipid A derivative, for example, monophosphoryl lipid A, a 3 deacylated monophosphoryl lipid A (3D-MPL), OM174, OM 294 DP or OM 197 MP-Ac DP and the like, alkyl glucosaminide phosphate (AGP), for example, AGP disclosed in WO 98/50399 or U.S. Pat. No. 6,303,347, or a salt of AGP as disclosed in U.S. Pat. No. 6,764,840, and a lipopolysaccharide derived from a Pantoea bacterium, a glucopyranosyl lipid, and sodium hyaluronate, but is not limited to them.

In a preferable aspect of the present invention, as the TLR4 ligand, lipopolysaccharides derived from genus Acetobacter (e.g. Acetobacter aceti, Acetobacter xylinum, Acetobacter orientalis etc.), genus Zymomonas (e.g. Zymomonas mobilis etc.), genus Xanthomonas (e.g. Xanthomonas campestris etc.), genus Enterobacter (e.g. Enterobacter cloacae etc.), and genus Pantoea (e.g. Pantoea agglomerans etc.) are preferable. Extracts derived from these lipopolysaccharides or purified lipopolysaccharides can be used as they are. In addition, for example, lipopolysaccharides (IP-PA1) derived from Pantoea agglomerans can be purchased from Funakoshi Corporation. In addition, in a preferable aspect of the present invention, the TLR4 ligand is a lipopolysaccharide derived from a Pantoea bacterium, glucopyranosyl lipid, and/or sodium hyaluronate.

As used herein, the term "TLR7 and/or TLR8 ligand" means a ligand of a Toll-like receptor (TLR) 7 and/or TLR8, and includes, for example, a single-stranded RNA, imiquimod, resiquimod (R848), TLR7-II and other compounds, for example, loxoribine and bropirimine, but is not limited to them.

In a preferable aspect of the present invention, the TLR7 and/or TLR8 ligand is imiquimod. Imiquimod is 1-(2-methylpropyl)-1H-imidazo[4,5-c]quinoline-4-amine of the formula:

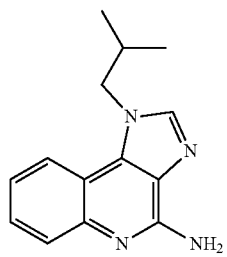 [SMILES: CC(C)Cn1cnc2c(N)nc3ccccc3c21]

and, for example, the characteristics and a production process thereof are described in JP 7-505883 A (Patent Document 2).

In other preferable aspect, the TLR7 and/or TLR8 ligand is resiquimod. Resiquimod is 4-amino-2-(ethoxymethyl)-α, α-dimethyl-1H-imidazo[4,5-c] quinoline-1-ethanol of the formula:

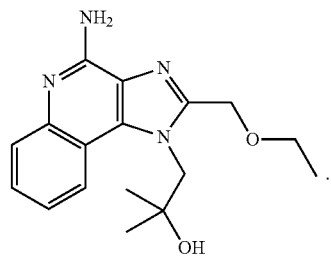 [SMILES: CCOCc1nc2c(N)nc3ccccc3c2n1CC(C)(C)O]

In other preferable aspect, the TLR7 and/or TLR8 ligand is TLR7-II. TLR7-II is represented by the formula:

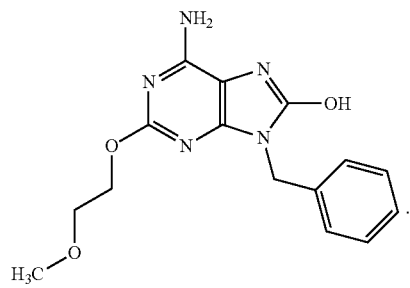 [SMILES: COCCOc1nc(N)c2nc(O)n(Cc3ccccc3)c2n1]

In other preferable aspect, the TLR7 and/or TLR8 ligand is bropirimine. Bropirimine is represented by the formula:

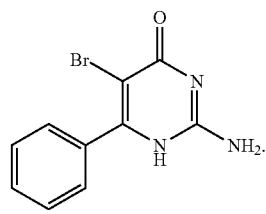 [SMILES: Nc1nc(=O)c(Br)c(-c2ccccc2)[nH]1]

As used herein, the term "TLR9 ligand" means a ligand of a Toll-like receptor (TLR) 9, and includes, for example, ODN1826 and the like. The TLR9 ligand used in the present invention may be an extract, a product or a synthetic product, and is not limited to them. In a preferable aspect of the present invention, the TLR9 ligand is ODN1826.

ODN1826 is an oligodeoxynucleotide consisting of the following sequence (SEQ ID No.: 4).

```
5'-tccatgacgttcctgacgtt-3'
```

As used herein, the term "TLR2/6 ligand" means a ligand of a heterodimer of Toll-like receptor (TLR) 2 and a Toll-like receptor (TLR) 6, and includes, for example, a diacylated lipoprotein derived from a cell wall of mycoplasma and a salt thereof, and these may be an extract, a product or a synthetic product, and are not limited to them. In a preferable aspect of the present invention, the TLR2/6 ligand is $Pam_2CSK_4$, MALP-2 and/or FSL-1.

$Pam_2CSK_4$ is represented by the following formula ("Ser-Lys-Lys-Lys-Lys" disclosed as SEQ ID NO: 9).

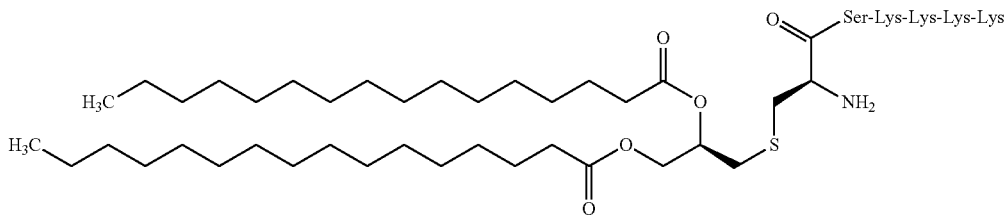

FSL-1 is represented by the following formula ("Gly-Asp-Pro-Lys-His-Pro-Lys-Ser-Phe" disclosed as SEQ ID NO: 10).

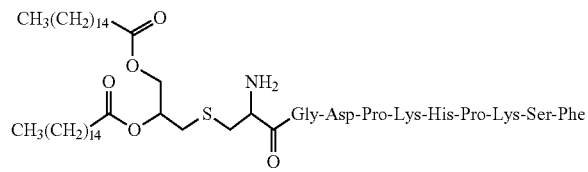

As used herein, the term "TLR5 ligand" means a ligand of a Toll-like receptor (TLR) 5, and includes, for example, flagellin and the like. The TLR5 ligand used in the present invention may be an extract, a product or a synthetic product, and is not limited to them. In a preferable aspect of the present invention, the TLR5 ligand is flagellin.

The Toll-like receptor (TLR) is a family of type I transmembrane proteins which initiates congenital immune response in which a specific cytokine, a specific chemokine and a growth factor participate, by in vivo activation thereof. All TLRs can activate a certain intracellular signal transmission molecule, for example, a nuclearity factor κB (NF-κB) and a mitogen-activated protein kinase (MAP kinase) or the like, while a specific population of a cytokine and a chemokine which are released seems to be inherent to each TLR. TLR3, 7, 8 and 9 include a subfamily of TLR which is present in an endosome fraction or a lysosome fraction of an immune cell (e.g. dendritic cell and monocyte). Specifically, TLR3 is expressed by a wide range of cells such as a dendritic cell and a fibroblast, TLR7 is expressed by a plasma cell-like dendritic cell, and is expressed by a monocyte to a lesser extent, TLR8 is expressed by a monocyte as well as a monocyte-derived dendritic cell and a myeloid dendritic cell, and TLR9 is expressed by a plasma cell-like dendritic cell. This subfamily mediates recognition of a microorganism nucleic acid (single-stranded RNA, double-stranded RNA, single-stranded DNA etc.). Agonists of TLR3, TLR7 and/or TLR8, and TLR9 stimulate production of a variety of inflammatory cytokines (including, for example, interleukin-6, interleukin-12, TNF-α, and interferon-γ). Such agonists also promote increase in expression of a costimulatory molecule (e.g. CD40, CD80, and CD86), a major histocompatibility complex molecule, and a chemokine receptor. Type I interferons (IFNα and IFNβ) are produced by a cell upon activation with TLR7 and/or TLR8 agonists.

As used herein, the term "cyclic dinucleotide" means a molecule in which two OH groups of a sugar part of two nucleotides produce an ester for each same phosphoric acid molecule, and thereby nucleotides are cyclized, and an analog thereof, and includes, for example, cyclic di-AMP (c-di-AMP), cyclic di-GMP (c-di-GMP), c-dGpGp, c-dGp-dGp, c-GpAp, c-GpCp, c-GpUp and the like, but is not limited to them. The cyclic dinucleotide activates a dendritic cell or a T cell. Further examples of the cyclic dinucleotide, use of them as an adjuvant, and a process for producing them are described in JP 2007-529531 A (Patent Document 3). In a preferable aspect of the present invention, the cyclic dinucleotide is cyclic di-GMP and/or cyclic di-AMP. The cyclic di-GMP has the formula:

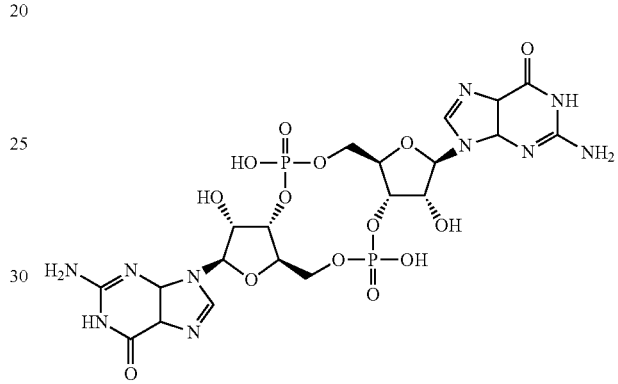

and a process for synthesizing it is described in Kawai et al., Nucleic Acids Research Suppl. 3: 103-4.

As used herein, the term "helper peptide" means any peptide which activates a helper T cell, and includes, for example, tubercle bacillus-derived helper peptide, measles virus-derived helper peptide, hepatitis B virus-derived helper peptide, hepatitis C virus-derived helper peptide, *Chlamydia trachomatis*-derived helper peptide, *Plasmodium falciparum* sporozoite-derived helper peptide, keyhole limpet haemocyanin-derived helper peptide, tetanus toxin-derived helper peptide, pertussis toxin-derived helper peptide, diphtheria toxin-derived helper peptide, cancer cell-derived helper peptide (e.g. WT1_332-347 helper peptide (described in Japanese Patent No. 4621142 "WT1-derived HLA-DR binding Antigen Peptide"), hWT1_35 helper peptide, hWT1_86 helper peptide, hWT1_294 helper peptide (above three kinds are described in WO 2010/123065 "Cancer Antigen Helper Peptide"), IMA-MMP-001 helper peptide, CEA-006 helper peptide, MMP-001 helper peptide, TGFBI-004 helper peptide, HER-2/neu (aa776-790) helper peptide, AE36 helper peptide, AE37 helper peptide, MET-005 helper peptide, BIR-002 helper peptide), and universal helper analog (e.g. PADRE). In a preferable aspect of the present invention, the helper peptide consists of 10 to 20 amino acids, preferably 12 to 19 amino acids, more preferably 13 to 18 amino acids. In a preferable aspect of the present invention, the helper peptide is Peptide-25, hWT1_35, PADRE, or WT_1332-347. Peptide-25 is a peptide of 15 amino acids consisting of a sequence Phe Gln Asp Ala Tyr Asn Ala Ala Gly Gly His Asn Ala Val Phe (SEQ ID No.: 5), corresponding to amino acid residues 240 to 254 of Ag85B which is one of main proteins secreted by human tubercle bacillus (*Mycobacterium tuber-*

*culosis*). Further, hWT1₃₅ is a peptide of 18 amino acids consisting of a sequence Trp Ala Pro Val Leu Asp Phe Ala Pro Pro Gly Ala Ser Ala Tyr Gly Ser Leu (shown as SEQ ID No.: 6 in the present application), described in WO 2010/123065 "Cancer Antigen Helper Peptide". PADRE is a peptide of 13 amino acids consisting of a sequence D-Ala Lys cyclohexyl-Ala Val Ala Ala Trp Thr Leu Lys Ala Ala D-Ala (shown as SEQ ID No.: 7 in the present application). WT1₃₃₂₋₃₄₇ is a peptide of 16 amino acids consisting of a sequence Lys Arg Tyr Phe Lys Leu Ser His Leu Gln Met His Ser Arg Lys His (shown as SEQ ID No.: 8 in the present application), described in Japanese Patent No. 4621142 "WT1-derived HLA-DR binding Antigen Peptide".

In addition, in the present invention, in place of the aforementioned helper peptides, or in combination therewith, peptides in which all or a part of amino acids of the helper peptides are modified by substitution, modification, or the like (hereinafter, referred to as "modified helper peptide") can also be used.

The modified helper peptides include, for example,
(a) a peptide consisting of an amino acid sequence in which one to several, for example, 1, 2, 3, 4 or 5 amino acids are substituted, deleted or added, in an amino acid sequence of the original helper peptide; and
(b) a peptide consisting of an amino acid sequence in which all or a part of amino acids, for example, one or more, for example, 1, 2, 3, 4, 5, 6, 7, 8, 9, 10, 11, 12, 13, 14, 15, 16, 17, or 18 amino acids are modified, in an amino acid sequence of the original helper peptide.

Examples of the "modification" of an amino acid which can be possessed by the modified helper peptide include, but are not limited to, aliphatic chain addition modification such as acetylation, alkylation such as methylation, glycosylation, hydroxylation, carboxylation, aldehydization, phosphorylation, sulfonylation, formylation, addition of fatty acid such as myristoylation, palmitoylation and stearoylation, octanoylation, esterification, amidation, deamidation, disulfide bond formation modification such as cystine modification, glutathione modification and thioglycolic acid modification, glycation, ubiquitination, succinimide formation glutamylation, prenylation and the like. In addition, the modified helper peptide may contain a combination of substitution, deletion or addition of one or more amino acids, and modification of one or more amino acids.

As used herein, the term "cyclooxygenase inhibitor" means a substance which inhibits the function of cyclooxygenase (COX). This is also referred to as "COX inhibitor" hereinafter. As COX inhibitors, there are a COX inhibitor which selectively acts on particular cyclooxygenase (e.g. COX-1 or COX-2), and a COX inhibitor having no selectivity. Examples of COX inhibitors which can be used in the present invention include etodolac, loxoprofen, celecoxib, valdecoxib, parecoxib, lumiracoxib, meloxicam, tenoxicam, diclofenac, mefenamic acid, tolfenamic acid, flufenamic acid, meclofenamic acid, niflumic acid, benzydamine, indobufen, triflusal, tolmetin, fenoprofen, tiaprofenic acid, felbinac, nepafenac, amfenac, pravadoline, zaltoprofen, sulindac, nabumetone, diflunisal, piroxicam, ibuprofen, naproxen, fenoprofen, aspirin, methyl salicylate, salicylamide, salsalate, aloxiprin, tolmetin, indomethacin, proglumetacine, acemetacin, flurbiprofen, pranoprofen, acetaminophen, floctafenine, lornoxicam, tenoxicam, tiaprofenic acid, oxaprozin, ketoprofen, dexketoprofen, dexibuprofen, alminoprofen, ketorolac, mofezolac, phenylbutazone, oxyphenylbutazone, ketophenylbutazone, feprazone, phenbutazone, ethenzamide, tiaramide, tinoridine, epirizole, emorfazone and a derivative thereof, as well as a pharmacologically acceptable salt thereof. In a preferable aspect of the present invention, the COX inhibitor is etodolac and/or loxoprofen.

Loxoprofen is represented by the formula:

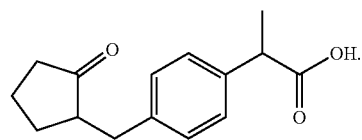 [SMILES: CC(C(=O)O)c1ccc(CC2CCCC2=O)cc1]

As used herein, the term "prostaglandin receptor antagonist" means a substance having the function of preventing prostaglandin from acting on a receptor, and includes, for example, an EP2 receptor antagonist, an EP4 receptor antagonist, a DP receptor antagonist, and an IP receptor antagonist.

As used herein, the term "EP2 receptor antagonist" means a substance having the function of preventing prostaglandin E2 from acting on an EP2 receptor. Examples of the EP2 receptor antagonist include AH6809 and a derivative thereof, as well as a pharmacologically acceptable salt thereof.

AH6809 is represented by the formula:

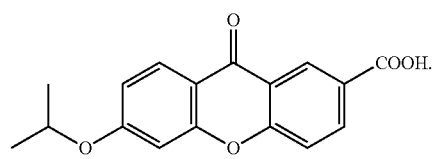 [SMILES: CC(C)Oc1ccc2c(=O)c3cc(C(=O)O)ccc3oc2c1]

As used herein, the term "EP4 receptor antagonist" means a substance having the function of preventing prostaglandin $E_2$ from acting on an EP4 receptor. Examples of the EP4 receptor antagonist include GW627368X and a derivative thereof, as well as a pharmacologically acceptable salt thereof.

GW627368X is represented by the formula:

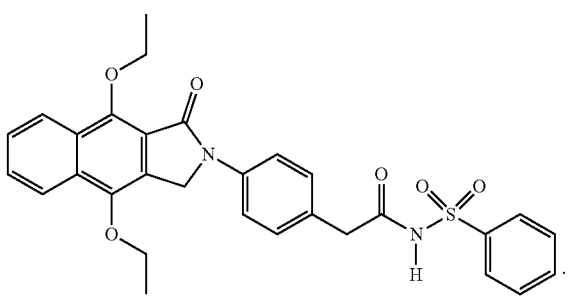 [SMILES: CCOc1c2c(c(OCC)c3ccccc13)C(=O)N(c1ccc(CC(=O)NS(=O)(=O)c3ccccc3)cc1)C2]

As used herein, the term "DP receptor antagonist" means a substance having the function of preventing prostaglandin $D_2$ from acting on a DP receptor. Examples of the DP receptor antagonist include S-5751, BWA868C and a derivative thereof, as well as a pharmacologically acceptable salt thereof.

BWA868C is represented by the formula:

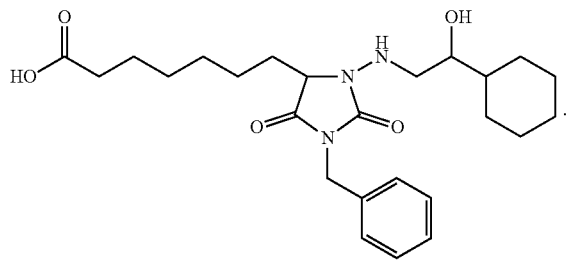 [SMILES: O=C(O)CCCCCCC1C(=O)N(Cc2ccccc2)C(=O)N1NCC(O)C1CCCCC1]

As used herein, the term "IP receptor antagonist" means a substance having the function of preventing prostaglandin I₂ from acting on an IP receptor. Examples of the IP receptor antagonist include RO1138452 and a derivative thereof, as well as a pharmacologically acceptable salt thereof.

RO1138452 is represented by the formula:

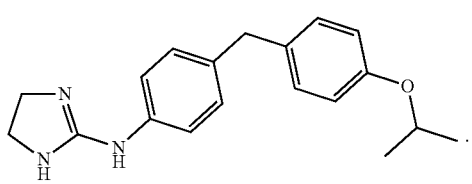 [SMILES: CC(C)Oc1ccc(Cc2ccc(NC3=NCCN3)cc2)cc1]

As used herein, the term "prostaglandin receptor agonist" means a substance having the function of acting on a prostaglandin receptor, and includes, for example, an EP3 receptor agonist.

As used herein, the term "EP3 receptor agonist" means a substance having the function of acting on an EP3 receptor. Examples of the EP3 receptor agonist include sulprostone, GR63799, cloprostenol, ONO-AE-248, carbacyclin, and a derivative thereof, as well as a pharmacologically acceptable salt thereof.

Sulprostone is represented by the formula:

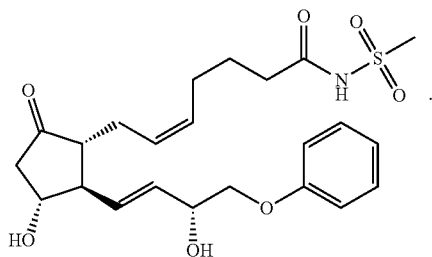 [SMILES: CS(=O)(=O)NC(=O)CCC/C=C\C[C@H]1C(=O)C[C@@H](O)[C@@H]1/C=C/[C@@H](O)COc1ccccc1]

As used herein, the term "TSLP production inhibitor" means a substance having the function of inhibiting production of TSLP. Since a drug which inhibits NF-κB is thought to indirectly inhibit the production of TSLP, it is included in this category. Examples of the TSLP production inhibitor include naringenin, berberine, resveratrol, luteolin, apigenin, chrysoeriol, velutin, rutin, hesperidin, quercetin, daidzein, genistein, noscapine, diindolylmethane, xanthone, parthenolide and a derivative thereof, as well as a pharmacologically acceptable salt thereof.

Berberine is represented by the formula:

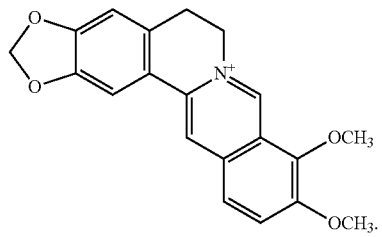 [SMILES: COc1ccc2cc3[n+](cc2c1OC)CCc1cc2c(cc1-3)OCO2]

As used herein, the term "adenylate cyclase inhibitor" means a substance having the function of inhibiting the activity of adenylate cyclase. Examples of the adenylate cyclase inhibitor include 2',5'-dideoxyadenosine, niacin, insulin, and a derivative thereof, as well as a pharmacologically acceptable salt thereof.

2',5'-Dideoxyadenosine is represented by the formula:

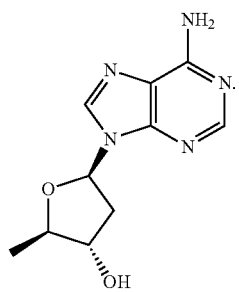 [SMILES: C[C@H]1O[C@@H](n2cnc3c(N)ncnc32)C[C@@H]1O]

As used herein, the term "omega-3 fatty acid" refers to an unsaturated fatty acid having a carbon-carbon double bond at the ω-3 position. Examples of the omega-3 fatty acid include eicosapentaenoic acid, α-linolenic acid, docosahexaenoic acid, and a derivative thereof, as well as a pharmacologically acceptable salt thereof.

Eicosapentaenoic acid is represented by the formula:

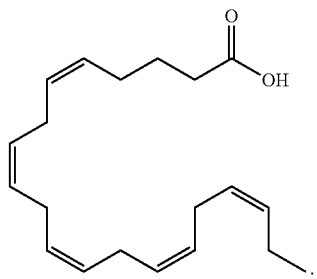 [SMILES: CC/C=C\C/C=C\C/C=C\C/C=C\C/C=C\CCCC(=O)O]

As used herein, the term "PPAR agonist" means a substance having the function of acting on a peroxisome proliferator-activated receptor, and includes, for example, a PPAR-α agonist, a PPAR-δ agonist, and a PPAR-γ agonist.

As used herein, the term "PPAR-α agonist" means a substance having the function of acting on an a type peroxisome proliferator-activated receptor. The term "PPAR-δ agonist" means a substance having the function of acting on a δ type peroxisome proliferator-activated receptor. The term "PPAR-γ agonist" means a substance having the function of acting on a γ type peroxisome proliferator-activated receptor. Examples of the PPAR-α agonist, and/or the PPAR-δ agonist, and/or the PPAR-γ agonist include clofibrate, fenofibrate, bezafibrate, ciprofibrate, etofibrate, telmisartan, oleyl ethanolamide, tetradecylthioacetic acid, troglitazone, pioglitazone, rosiglitazone, balaglitazone, rivoglitazone, ciglitazone, darglitazone, edaglitazone, netoglitazone, indeglitazar, tesaglitazar, muraglitazar, aleglitazar, and a derivative thereof, as well as a pharmacologically acceptable salt thereof.

Clofibrate is represented by the formula:

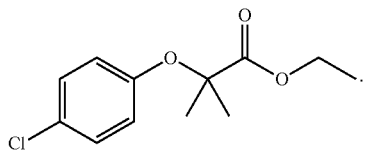 [SMILES: CCOC(=O)C(C)(C)Oc1ccc(Cl)cc1]

As used herein, the term "dopamine receptor antagonist" means a substance having the function of preventing dopamine from acting on a receptor, and includes, for example, a D1 receptor antagonist, and a D5 receptor antagonist.

As used herein, the term "D1 receptor antagonist" means a substance having the function of preventing dopamine from acting on a D1 receptor. Examples of the D1 receptor antagonist include benzazepine, fenoldopam, lorcaserin, SCH23390, SCH39166, LE300 and a derivative thereof, as well as a pharmacologically acceptable salt thereof.

Benzazepine is represented by the formula:

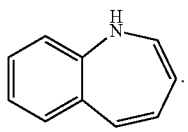 [SMILES: C1=CNc2ccccc2C=C1]

As used herein, the term "D5 receptor antagonist" means a substance having the function of preventing dopamine from acting on a D5 receptor. Examples of the D5 receptor antagonist include SCH39166 and a derivative thereof, as well as a pharmacologically acceptable salt thereof.

SCH39166 is represented by the formula:

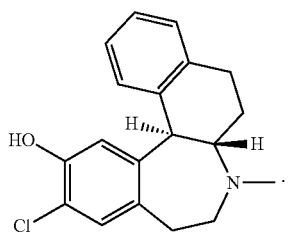 [SMILES: CN1CCc2cc(Cl)c(O)cc2[C@H]2c3ccccc3CC[C@@H]21]

As used herein, the term "dopamine receptor agonist" means a substance having the function of acting on a dopamine receptor, and includes, for example, a D2 receptor agonist, a D3 receptor agonist, and a D4 receptor agonist.

As used herein, the term "D2 receptor agonist" means a substance having the function of acting on a D2 receptor. Examples of the D2 receptor agonist include cabergoline, bromocriptine, pergolide, ropinirole, talipexole, aripiprazole, lurasidone, and a derivative thereof, as well as a pharmacologically acceptable salt thereof.

Ropinirole is represented by the formula:

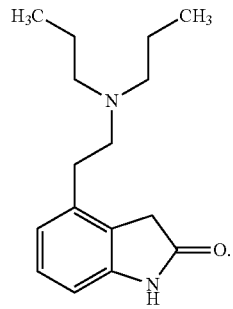 [SMILES: CCCN(CCC)CCc1cccc2c1CC(=O)N2]

As used herein, the term "D3 receptor agonist" means a substance having the function of acting on a D3 receptor. Examples of the D3 receptor agonist include piribedil, rotigotine, PD1289077, OH-DPAT and a derivative thereof, as well as a pharmacologically acceptable salt thereof.

Rotigotine is represented by the formula:

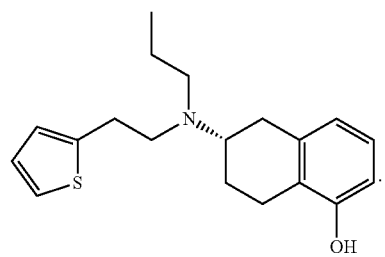 [SMILES: CCCN(CCc1cccs1)[C@H]1CCc2c(O)cccc2C1]

As used herein, the term "D4 receptor agonist" means a substance having the function of acting on a D4 receptor. Examples of the D4 receptor agonist include flibanserin, ABT724, PD168077, CP226269 and a derivative thereof, as well as a pharmacologically acceptable salt thereof.

Flibanserin is represented by the formula:

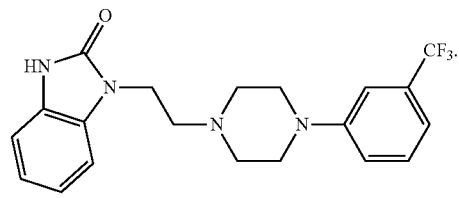 [SMILES: O=c1[nH]c2ccccc2n1CCN1CCN(c2cccc(C(F)(F)F)c2)CC1]

As used herein, the term "histamine receptor antagonist" means a substance having the function of preventing histamine from acting on a receptor, and includes, for example, a H1 receptor antagonist, and a H2 receptor antagonist.

As used herein, the term "H1 receptor antagonist" means a substance having the function of preventing histamine from acting on a H1 receptor. Examples of the H1 receptor antagonist include ketanserin, thonzylamine, mepyramine, tripelenamine, dimethindene, clemastine, bamipine, isothipendyl, chlorphenoxamine, dimetotiazine, chlorpromazine, hydroxyzine, opipramol, betahistine, cinnarizine, levocabastine, antazoline, diphenylpyraline, carbinoxamine, doxylamine, alimemazine, cyclizine, meclozine, levocetirizine, cyproheptadine, phenindamine, triprolidine, azatadine, astemizole, terfenadine, acrivastine, ebastine, desloratadine, rupatadine, bilastine, mizolastine, noberastine, rocastine, temelastine, bepotastine, diphenhydramine, chlorpheniramine, ketotifen, promethazine, cyproheptadine, epinastine, olopatadine, bepotastine, astemizole, emedastine, mequitazine, oxatomide, loratadine, fexofenadine, cetirizine, azelastine, and a derivative thereof, as well as a pharmacologically acceptable salt thereof.

Diphenhydramine is represented by the formula:

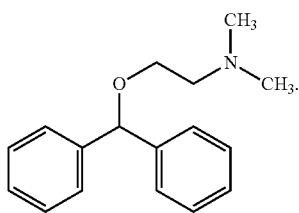 [SMILES: CN(C)CCOC(c1ccccc1)c1ccccc1]

As used herein, the term "H2 receptor antagonist" means a substance having the function of preventing histamine from acting on a H2 receptor. Examples of the H2 receptor antagonist include cimetidine, ranitidine, famotidine, nizatidine, roxatidine, lafutidine, and a derivative thereof, as well as a pharmacologically acceptable salt thereof.

Famotidine is represented by the formula:

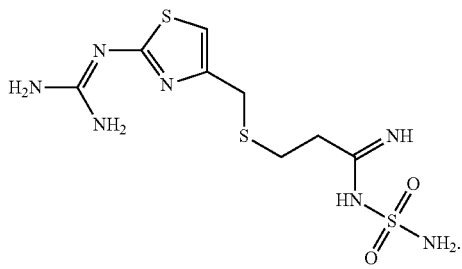 [SMILES: N=C(CCSCc1csc(N=C(N)N)n1)NS(N)(=O)=O]

As used herein, the term "histamine receptor agonist" means a substance having the function of acting on a histamine receptor, and includes, for example, a H1 receptor agonist, a H3 receptor agonist, and a H4 receptor agonist.

As used herein, the term "H1 receptor agonist" means a substance having the function of acting on a H1 receptor. Examples of the H1 receptor agonist include 2-pyridylethylamine, 2-thiazolylethylamine and a derivative thereof, as well as a pharmacologically acceptable salt thereof.

2-Pyridylethylamine is represented by the formula:

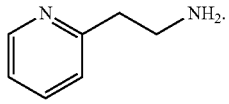

As used herein, the term "H3 receptor agonist" means a substance having the function of acting on a H3 receptor. Examples of the H3 receptor agonist include immethridine, imetit, immepip, α-methylhistamine, proxyfan, and a derivative thereof, as well as a pharmacologically acceptable salt thereof.

Proxyfan is represented by the formula:

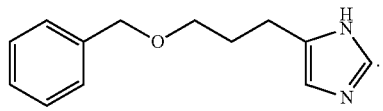 [SMILES: c1ccc(COCCCc2cnc[nH]2)cc1]

As used herein, the term "H4 receptor agonist" means a substance having the function of acting on a H4 receptor. Examples of the H4 receptor agonist include 4-methylhistamine, VUF8430, immepip and a derivative thereof, as well as a pharmacologically acceptable salt thereof.

4-Methylhistamine is represented by the formula:

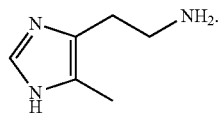

As used herein, the term "serotonin receptor antagonist" means a substance having the function of preventing serotonin from acting on a receptor, and includes, for example, a 5-HT2 receptor antagonist, a 5-HT4 receptor antagonist, a 5-HT6 receptor antagonist, and a 5-HT7 receptor antagonist.

As used herein, the term "5-HT2 receptor antagonist" means a substance having the function of preventing serotonin from acting on a 5-HT2 receptor. Examples of the 5-HT2 receptor antagonist include pizotifen, risperidone, olanzapine, quetiapine, aripiprazole, blonanserin, clozapine, paliperidone, ritanserin, yohimbine, mesulergine, agomelatine, cyclobenzaprine, sarpogrelate, methysergide, ketanserin, and a derivative thereof, as well as a pharmacologically acceptable salt thereof.

Olanzapine is represented by the formula:

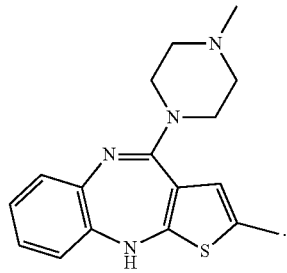 [SMILES: Cc1cc2c(s1)Nc1ccccc1N=C2N1CCN(C)CC1]

As used herein, the term "5-HT4 receptor antagonist" means a substance having the function of preventing serotonin from acting on a 5-HT4 receptor. Examples of the 5-HT4 receptor antagonist include piboserod, GR113808, GR125487, RS39604, SB204070 and a derivative thereof, as well as a pharmacologically acceptable salt thereof.

Piboserod is represented by the formula:

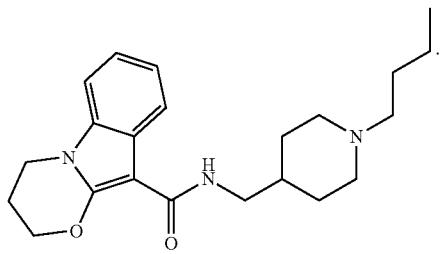 [SMILES: CCCCN1CCC(CNC(=O)c2c3n(c4ccccc24)CCCO3)CC1]

As used herein, the term "5-HT6 receptor antagonist" means a substance having the function of preventing serotonin from acting on a 5-HT6 receptor. Examples of the 5-HT6 receptor antagonist include cerlapirdine, clozapine and a derivative thereof, as well as a pharmacologically acceptable salt thereof.

Cerlapirdine is represented by the formula:

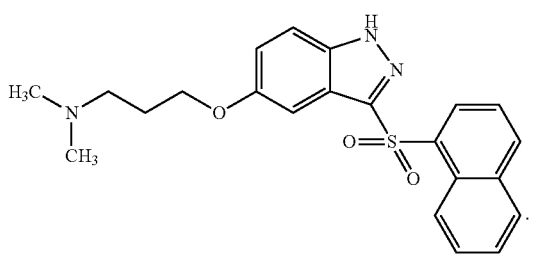 [SMILES: CN(C)CCCOc1ccc2[nH]nc(S(=O)(=O)c3cccc4ccccc34)c2c1]

As used herein, the term "5-HT7 receptor antagonist" means a substance having the function of preventing serotonin from acting on a 5-HT7 receptor. Examples of the 5-HT7 receptor antagonist include lurasidone, metergoline, and a derivative thereof, as well as a pharmacologically acceptable salt thereof.

Metergoline is represented by the formula:

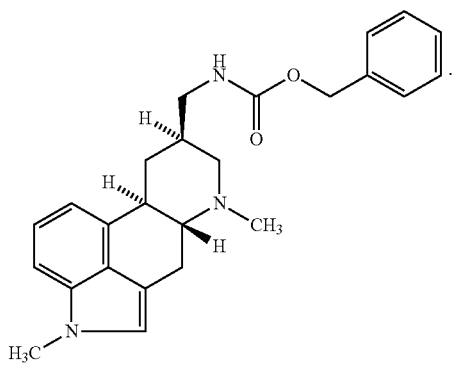 [SMILES: CN1C[C@H](CNC(=O)OCc2ccccc2)C[C@@H]2c3cccc4c3c(cn4C)C[C@H]21]

As used herein, the term "serotonin receptor agonist" means a substance having the function of acting on a serotonin receptor, and includes, for example, a 5-HT1 receptor agonist, and a 5-HT2 receptor agonist.

As used herein, the term "5-HT1 receptor agonist" means a substance having the function of acting on a 5-HT1 receptor. Examples of the 5-HT1 receptor agonist include piclozotan, tandospirone, sumatriptan, zolmitriptan, eletriptan, rizatriptan, naratriptan, almotriptan, frovatriptan, avitriptan, ergotamine, ergot alkaloid, and a derivative thereof, as well as a pharmacologically acceptable salt thereof.

Zolmitriptan is represented by the formula:

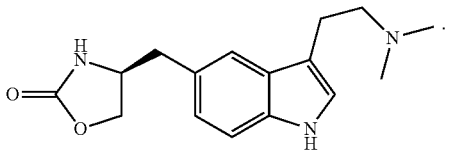 [SMILES: CN(C)CCc1c[nH]c2ccc(C[C@H]3COC(=O)N3)cc12]

As used herein, the term "5-HT2 receptor agonist" means a substance having the function of acting on a 5-HT2 receptor. Examples of the 5-HT2 receptor agonist include α-methyl-5-HT, agomelatine, norfenfluramine, meta-chlorophenylpiperazine and a derivative thereof, as well as a pharmacologically acceptable salt thereof.

Agomelatine is represented by the formula:

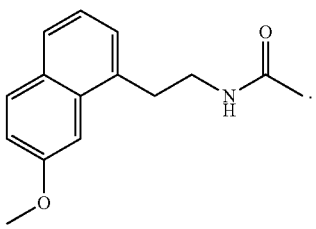 [SMILES: COc1ccc2cccc(CCNC(C)=O)c2c1]

As used herein, the term "vasopressin receptor antagonist" means a substance having the function of preventing vasopressin from acting on a receptor, and includes, for example, a V2 receptor antagonist.

As used herein, the term "V2 receptor antagonist" means a substance having the function of preventing vasopressin from acting on a V2 receptor. Examples of the V2 receptor antagonist include tolvaptan, mozavaptan, conivaptan, lixivaptan, and a derivative thereof, as well as a pharmacologically acceptable salt thereof.

Mozavaptan is represented by the formula:

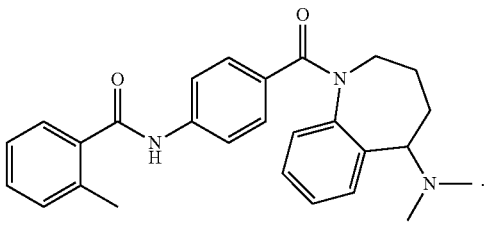 [SMILES: Cc1ccccc1C(=O)Nc1ccc(C(=O)N2CCCC(N(C)C)c3ccccc32)cc1]

As used herein, the term "vasopressin receptor agonist" means a substance having the function of acting on a vasopressin receptor, and includes, for example, a V1 receptor agonist.

As used herein, the term "V1 receptor agonist" means a substance having the function of acting on a V1 receptor. Examples of the V1 receptor agonist include vasopressin, felypressin, desmopressin, lypressin, terlipressin, ornipressin, argipressin, and a derivative thereof, as well as a pharmacologically acceptable salt thereof.

Desmopressin is represented by the formula:

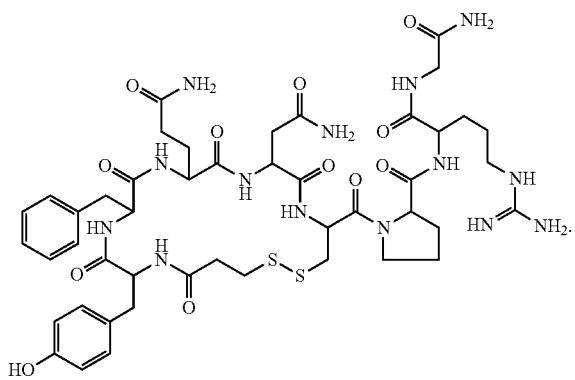 [SMILES: N=C(N)NCCCC(NC(=O)C1CCCN1C(=O)C1CSSCCC(=O)NC(Cc2ccc(O)cc2)C(=O)NC(Cc2ccccc2)C(=O)NC(CCC(N)=O)C(=O)NC(CC(N)=O)C(=O)N1)C(=O)NCC(N)=O]

As used herein, the term "muscarine receptor antagonist" means a substance having the function of preventing acetylcholine from acting on a muscarine receptor, and includes, for example, a M1 receptor antagonist, a M3 receptor antagonist, and a M5 receptor antagonist.

As used herein, the term "M1 receptor antagonist" means a substance having the function of preventing acetylcholine from acting on a M1 receptor. The term "M3 receptor antagonist" means a substance having the function of preventing acetylcholine from acting on a M3 receptor. The term "M5 receptor antagonist" means a substance having the function of preventing acetylcholine from acting on a M5 receptor. Examples of the M1 receptor antagonist, and/or the M3 receptor antagonist, and/or the M5 receptor antagonist include pirenzepine, atropine, trimebutine, piperidolate, oxybutynin, tropicamide, propiverine, tolterodine, solifenacin, darifenacin, imidafenacin, oxyphencyclimine, tiotropium bromide, esoxybutynin, tiquizium, and a derivative thereof, as well as a pharmacologically acceptable salt thereof.

Oxybutynin is represented by the formula:

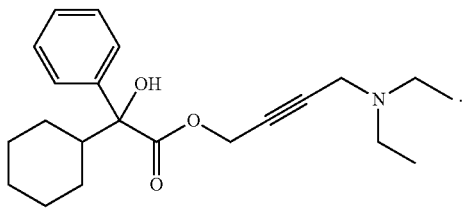 [SMILES: CCN(CC)CC#CCOC(=O)C(O)(c1ccccc1)C1CCCCC1]

As used herein, the term "muscarine receptor agonist" means a substance having the function of acting on a muscarine receptor, and includes, for example, a M1 receptor agonist, a M2 receptor agonist, a M3 receptor agonist, a M4 receptor agonist, and a M5 receptor agonist.

As used herein, the term "M1 receptor agonist" means a substance having the function of acting on a M1 receptor. The term "M2 receptor agonist" means a substance having the function of acting on a M2 receptor. The term "M3 receptor agonist" means a substance having the function of acting on a M3 receptor. The term "M4 receptor agonist" means a substance having the function of acting on a M4 receptor. The term "M5 receptor agonist" means a substance having the function of acting on a M5 receptor. Examples of the M1 receptor agonist, and/or the M2 receptor agonist, and/or the M3 receptor agonist, and/or the M4 receptor agonist, and/or the M5 receptor agonist include acetylcholine, aceclidine, alvameline, talsaclidine, xanomeline, pilocarpine, cevimeline, bethanechol, mazaticol, muscarine, and a derivative thereof, as well as a pharmacologically acceptable salt thereof.

Bethanechol is represented by the formula:

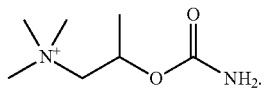

As used herein, the term "adrenalin receptor antagonist" means a substance having the function of preventing adrenalin from acting on a receptor, and includes, for example, an $\alpha 1$ receptor antagonist, a $\beta 1$ receptor antagonist, a $\beta 2$ receptor antagonist, and a $\beta 3$ receptor antagonist.

As used herein, the term "$\alpha 1$ receptor antagonist" means a substance having the function of preventing adrenalin from acting on an $\alpha 1$ receptor. Examples of the $\alpha 1$ receptor antagonist include prazosin, doxazosin, bunazosin, trimazosin, alfuzosin, silodosin, terazosin, tamusulosin, and a derivative thereof, as well as a pharmacologically acceptable salt thereof.

Tamusulosin is represented by the formula:

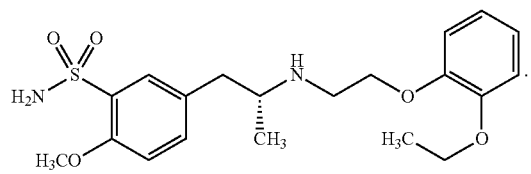 [SMILES: CCOc1ccccc1OCCN[C@H](C)Cc1ccc(OC)c(S(N)(=O)=O)c1]

As used herein, the term "$\beta 1$ receptor antagonist" means a substance having the function of preventing adrenalin from acting on a $\beta 1$ receptor. The term "$\beta 2$ receptor antagonist" means a substance having the function of preventing adrenalin from acting on a $\beta 2$ receptor. The term "$\beta 3$ receptor antagonist" means a substance having the function of preventing adrenalin from acting on a $\beta 3$ receptor. Examples of the $\beta 1$ receptor antagonist, and/or the $\beta 2$ receptor antagonist, and/or the $\beta 3$ receptor antagonist include bopindolol, pindolol, timolol, dichloroisoprenaline, alprenolol, carteolol, indenolol, bunitrolol, penbutolol, propranolol, nadolol, nipradilol, tilisolol, acebutolol, celiprolol, metoprolol, atenolol, bisoprolol, betaxolol, practolol, bevantolol, butoxamine, carvedilol, amosulalol, arotinolol, labetalol, and a derivative thereof, as well as a pharmacologically acceptable salt thereof.

Propranolol is represented by the formula:

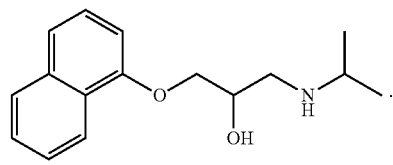 [SMILES: CC(C)NCC(O)COc1cccc2ccccc12]

As used herein, the term "angiotensin receptor agonist" means a substance having the function of acting on an angiotensin receptor, and includes, for example, an AT2 receptor agonist.

As used herein, the term "adrenalin receptor agonist" means a substance having the function of acting on an adrenalin receptor, and includes, for example, an α1 receptor agonist, and an α2 receptor agonist.

As used herein, the term "α1 receptor agonist" means a substance having the function of acting on an α1 receptor. The term "α2 receptor agonist" means a substance having the function of acting on an α2 receptor. Examples of the α1 receptor agonist, and/or the α2 receptor agonist include norepinephrine, norfenefrine, etilefrine, naphazoline, phenylephrine, midodrine, methoxamine, oxedrine, metaraminol, arbutamine, ephedrine, oxymetazoline, tetryzoline, xylometazoline, tramazoline, pseudoephedrine, dipivefrine, amidephrine, methylephedrine, rilmenidine, brimonidine, medetomidine, xylazine, tizanidine, guanfacine, methyldopa, guanabenz, and a derivative thereof, as well as a pharmacologically acceptable salt thereof.

Xylazine is represented by the formula:

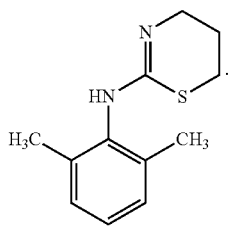

As used herein, the term "angiotensin receptor agonist" means a substance having the function of acting on an angiotensin receptor, and includes, for example, an AT2 receptor agonist.

As used herein, the term "AT2 receptor agonist" means a substance having the function of acting on an AT2 receptor. Examples of the AT2 receptor agonist include novokinin, angiotensin and a derivative thereof, as well as a pharmacologically acceptable salt thereof.

Angiotensin is represented by the formula:

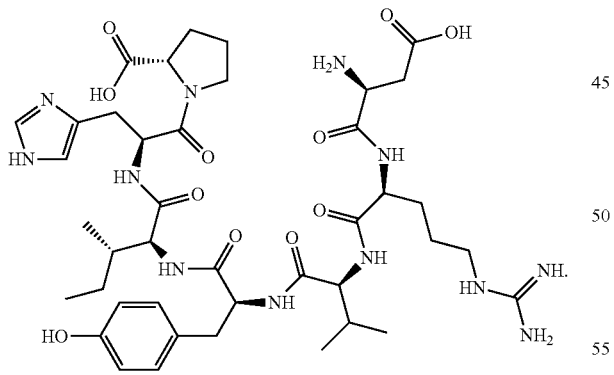

As used herein, the term "GABA receptor agonist" means a substance having the function of acting on a GABA receptor, and includes, for example, a $GABA_B$ receptor agonist.

As used herein, the term "$GABA_B$ receptor agonist" means a substance having the function of acting on a $GABA_B$ receptor. Examples of the $GABA_B$ receptor agonist include baclofen, γ-aminobutyric acid, arbaclofen and a derivative thereof, as well as a pharmacologically acceptable salt thereof.

Baclofen is represented by the formula:

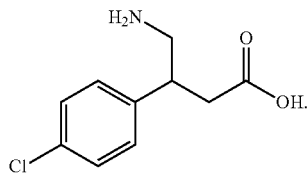 [SMILES: NCC(CC(=O)O)c1ccc(Cl)cc1]

As used herein, the term "thrombin receptor antagonist" means a substance having the function of preventing thrombin from acting on a receptor, and includes, for example, a PAR-1 receptor antagonist.

As used herein, the term "PAR-1 receptor antagonist" means a substance having the function of preventing thrombin from acting on a PAR-1 receptor. Examples of the PAR-1 receptor antagonist include vorapaxar, atopaxar, FR171113, RWJ56110, dabigatran, dabigatran etexilate, melagatran, ximelagatran, hirudin, hirulog, argatroban and a derivative thereof, as well as a pharmacologically acceptable salt thereof.

Vorapaxar is represented by the formula:

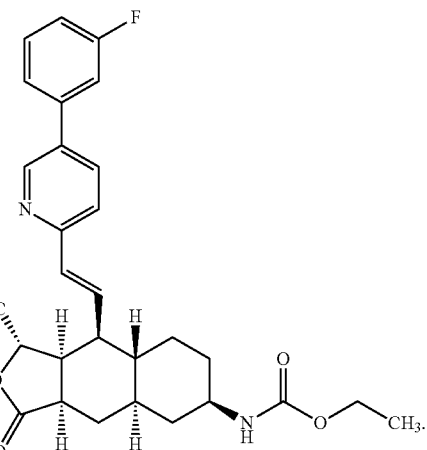

As used herein, the term "thrombin receptor agonist" means a substance having the function of acting on a thrombin receptor, and includes, for example, a PAR-1 receptor agonist.

As used herein, the term "PAR-1 receptor agonist" means a substance having the function of acting on a PAR-1 receptor. Examples of the PAR-1 receptor agonist include TRAP-6, TRAP-14, NAT6-NH$_2$ and a derivative thereof, as well as a pharmaceutically acceptable salt thereof.

TRAP-6 is represented by the formula:

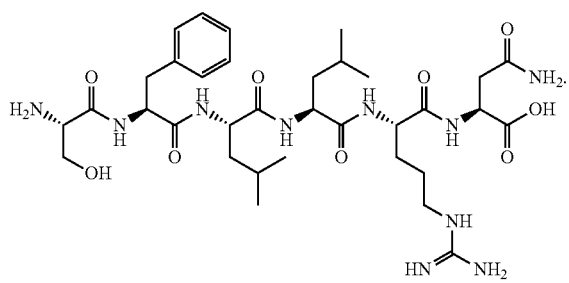 [SMILES: CC(C)C[C@H](NC(=O)[C@H](CC(C)C)NC(=O)[C@H](Cc1ccccc1)NC(=O)[C@@H](N)CO)C(=O)N[C@@H](CCCNC(=N)N)C(=O)N[C@@H](CC(N)=O)C(=O)O]

As used herein, the term "opioid receptor agonist" means a substance having the function of acting on an opioid receptor. Examples of the opioid receptor agonist include trimebutine, alvimopan, morphine, oxycodone, dihydrocodeine, diamorphine, pethidine, pentazocine, buprenorphine, butorphanol, nalbuphine, tilidine, dezocine, meptazinol, tapentadol, naltrexone, methadone, ethylmorphine, hydrocodone, acetyldihydrocodeine, nalorphine, loperamide, remoxipride, opipramol, and a derivative thereof, as well as a pharmacologically acceptable salt thereof.

Buprenorphine is represented by the formula:

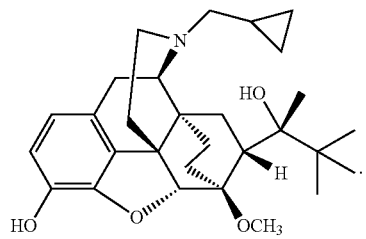

As used herein, the term "leukotriene receptor antagonist" means a substance having the function of preventing leukotriene from acting on a receptor, and includes, for example, a CysLT1 receptor antagonist, and a CysLT2 receptor antagonist.

As used herein, the term "CysLT1 receptor antagonist" means a substance having the function of preventing leukotriene from acting on a CysLT1 receptor. The term "CysLT2 receptor antagonist" means a substance having the function of preventing leukotriene from acting on a CysLT2 receptor. Examples of the CysLT1 receptor antagonist, and/or the CysLT2 receptor antagonist include montelukast, zafirlukast, pranlukast, and a derivative thereof, as well as a pharmacologically acceptable salt thereof. Examples of the pharmacologically acceptable salt of montelukast include montelukast sodium and the like.

Montelukast sodium is represented by the formula:

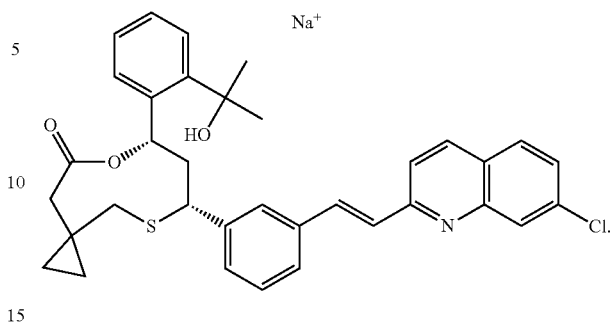

As used herein, the term "leukotriene receptor agonist" means a substance having the function of acting on a leukotriene receptor, and includes, for example, a BLT receptor agonist.

As used herein, the term "BLT receptor agonist" means a substance having the function of acting on a BLT receptor. Examples of the BLT receptor agonist include leukotriene B4, CAY10583 and a derivative thereof, as well as a pharmacologically acceptable salt thereof.

Leukotriene B4 is represented by the formula:

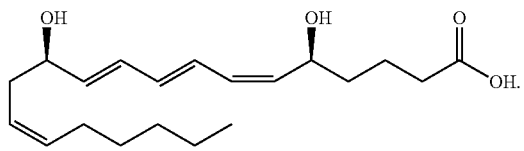 [SMILES: CCCCC/C=C\C[C@@H](O)/C=C/C=C/C=C\[C@@H](O)CCCC(=O)O]

As used herein, the term "ADP receptor agonist" means a substance having the function of acting on an ADP receptor. Examples of the ADP receptor agonist include adenosine diphosphate, and a derivative thereof, as well as a pharmacologically acceptable salt thereof.

Adenosine diphosphate is represented by the formula:

[Chemical formula 50]

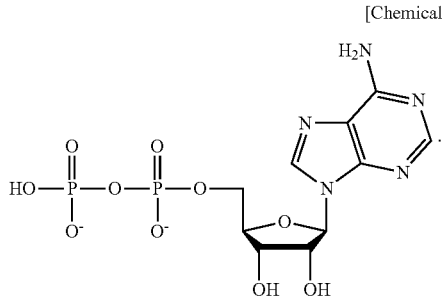

As used herein, the term "melatonin receptor agonist" means a substance having the function of acting on a melatonin receptor. Examples of the melatonin receptor agonist include melatonin, perlapine, tasimelteon, and a derivative thereof, as well as a pharmacologically acceptable salt thereof.

Melatonin is represented by the formula:

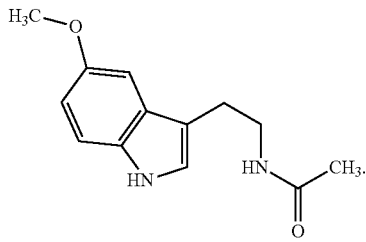 [SMILES: COc1ccc2[nH]cc(CCNC(C)=O)c2c1]

As used herein, the term "somatostatin receptor agonist" means a substance having the function of acting on a somatostatin receptor. Examples of the somatostatin receptor agonist include somatostatin, somatostatin-14, octreotide, and a derivative thereof, as well as a pharmacologically acceptable salt thereof.

Octreotide is represented by the formula:

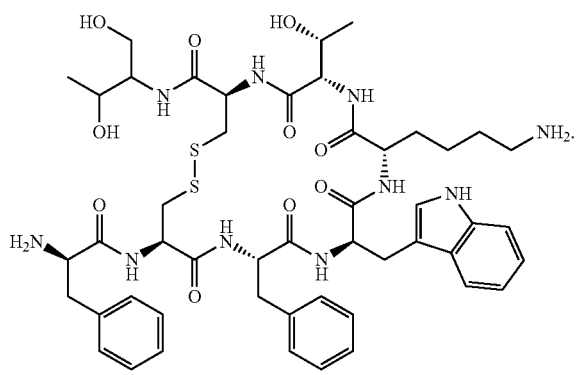 [SMILES: CC(O)C(CO)NC(=O)[C@@H]1CSSC[C@H](NC(=O)[C@H](N)Cc2ccccc2)C(=O)N[C@@H](Cc2ccccc2)C(=O)N[C@H](Cc2c[nH]c3ccccc23)C(=O)N[C@@H](CCCCN)C(=O)N[C@@H]([C@@H](C)O)C(=O)N1]

As used herein, the term "cannabinoid receptor agonist" means a substance having the function of acting on a cannabinoid receptor. Examples of the cannabinoid receptor agonist include dronabinol, nabilone, levonantradol, otenabant, GW833972A, GW405833, and a derivative thereof, as well as a pharmacologically acceptable salt thereof.

Dronabinol is represented by the formula:

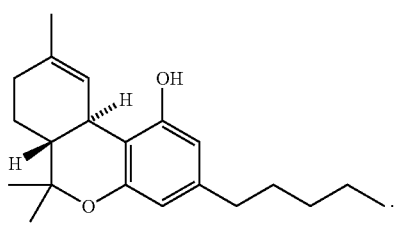 [SMILES: CCCCCc1cc(O)c2c(c1)OC(C)(C)[C@@H]1CCC(C)=C[C@@H]21 ; "."]

As used herein, the term "sphingosine-1 phosphate receptor agonist" means a substance having the function of acting on a sphingosine-1 phosphate receptor. Examples of the sphingosine-1 phosphate receptor agonist include fingolimod, ponesimod, RPC-1063, ONO-4641, SEW2871, sphingosine-1 phosphate and a derivative thereof, as well as a pharmacologically acceptable salt thereof.

Fingolimod is represented by the formula:

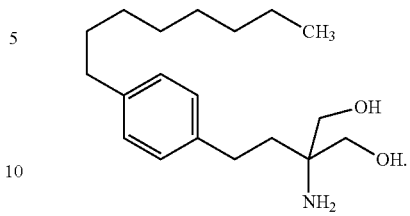

As used herein, the term "metabotropic glutamate receptor agonist" means a substance having the function of acting on a metabotropic glutamate receptor, and includes, for example, an mGluR2 receptor agonist, an mGluR3 receptor agonist, an mGluR4 receptor agonist, an mGluR6 receptor agonist, an mGluR7 receptor agonist, and an mGluR8 receptor agonist.

As used herein, the term "mGluR2 receptor agonist" means a substance having the function of acting on an mGluR2 receptor. The term "mGluR3 receptor agonist" means a substance having the function of acting on an mGluR3 receptor. The term "mGluR4 receptor agonist" means a substance having the function of acting on an mGluR4 receptor. The term "mGluR6 receptor agonist" means a substance having the function of acting on an mGluR6 receptor. The term "mGluR7 receptor agonist" means a substance having the function of acting on an mGluR7 receptor. The term "mGluR8 receptor agonist" means a substance having the function of acting on an mGluR8 receptor. Examples of the mGluR2 receptor agonist, and/or the mGluR3 receptor agonist, and/or the mGluR4 receptor agonist, and/or the mGluR6 receptor agonist, and/or the mGluR7 receptor agonist, and/or the mGluR8 receptor agonist include VUO361737, VU0155041, biphenylindanone A, PBDA, L-Aβ4, and a derivative thereof, as well as a pharmacologically acceptable salt thereof.

VUO361737 is represented by the formula:

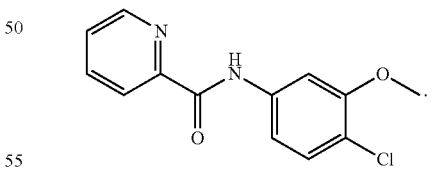

As used herein, the term "phospholipase A2 inhibitor" means a substance having the function of inhibiting the activity of phospholipase A2. Examples of the phospholipase A2 inhibitor include glycyrrhizic acid, glycyrrhetic acid, and a derivative thereof, as well as a pharmacologically acceptable salt thereof.

Glycyrrhetic acid is represented by the formula:

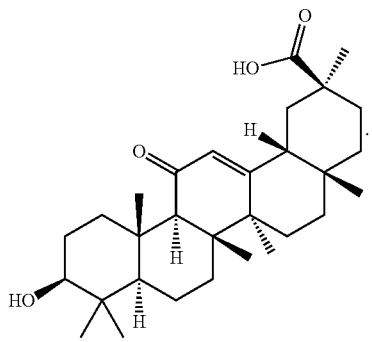

As used herein, the term "TGF-β production inhibitor" means a substance having the function of inhibiting production of TGF-β. Examples of the TGF-β production inhibitor include pirfenidone, tranilast, and a derivative thereof, as well as a pharmacologically acceptable salt thereof.

Pirfenidone is represented by the formula:

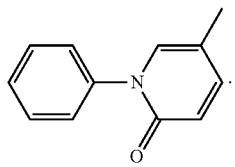

As used herein, the term "Th2 cytokine inhibitor" means a substance having the function of inhibiting production of a Th2 cytokine such as IL-4 and IL-5. Examples of the Th2 cytokine inhibitor include suplatast and a derivative thereof, as well as a pharmacologically acceptable salt thereof. Examples of the pharmacologically acceptable salt of suplatast include suplatast tosylate. In a preferable aspect of the present invention, the Th2 cytokine inhibitor is suplatast tosylate.

Suplatast tosylate is represented by the formula:

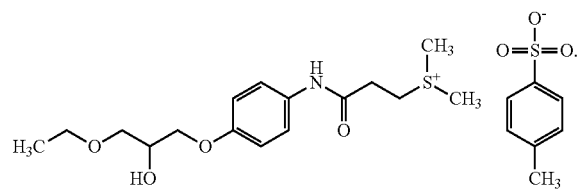 [SMILES: CCOCC(O)COc1ccc(NC(=O)CC[S+](C)C)cc1 ; Cc1ccc(S(=O)(=O)[O-])cc1]

As used herein, the "pharmacologically acceptable acid" as a second cellular immunity induction promoter that can be incorporated into the tape preparation of the present invention means an acid which does not have any adverse action on the subject of administration and does not lose the pharmacological activity of the components in the tape preparation. According to a preferred aspect of the present invention, the pharmacologically acceptable acid is an organic acid; more preferably an organic compound containing carboxyl group or an organic compound containing sulfonate group; even more preferably a saturated or unsaturated, linear or branched fatty acid having a saturated linear moiety with 8 to 20 carbon atoms, lactic acid, malic acid, salicylic acid, maleic acid, citric acid, or an organic compound containing sulfonate group; still more preferably a saturated or unsaturated, linear or branched fatty acid having a saturated linear moiety with 8 to 16 carbon atoms, lactic acid, malic acid, salicylic acid, maleic acid, citric acid, an organic compound containing sulfonate group; and even more preferably a fatty acid selected from the group consisting of decanoic acid, lauric acid, myristic acid, isostearic acid and oleic acid, or lactic acid, salicylic acid, citric acid or methanesulfonic acid.

As used herein, the "pharmacologically acceptable salt" that can be incorporated into the tape preparation of the present invention means a salt which does not have any adverse action on the subject of administration, and does not lose the pharmacological activity of the components in the tape preparation. Examples include, but are not limited to, inorganic acid salts (for example, hydrochlorides and phosphates), organic acid salts (for example, acetates, phthalates, and TFA salts), metal salts (alkali metal salts (for example, sodium salts and potassium salts), alkaline earth metal salts (for example, calcium salts and magnesium salts), aluminum salts, and the like), amine salts (triethylamine salts, benzylamine salts, diethanolamine salts, t-butylamine salts, dicyclohexylamine salts, arginine salts, dimethylammonium salts, ammonium salts, and the like).

As used herein, the term "immunomodulatory small molecule drug" means a substance which activates or suppresses immune cells such as a T cell, a NK cell, a macrophage and the like, and which does not correspond to any of the aforementioned TLR ligand, cyclic dinucleotide, helper peptide, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-β production inhibitor, and Th2 cytokine inhibitor. Examples of the immunomodulatory small molecule drug include bestatin, pidotimod, levamisole, golotimod, forphenicinol, and a derivative thereof, as well as a pharmacologically acceptable salt thereof. Examples of the pharmacologically acceptable salt of levamisole include levamisole hydrochloride.

Bestatin is represented by the formula:

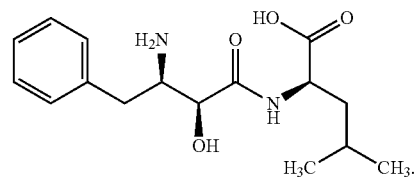 [SMILES: CC(C)C[C@@H](NC(=O)[C@@H](O)[C@H](N)Cc1ccccc1)C(=O)O]

Pidotimod is represented by the formula:

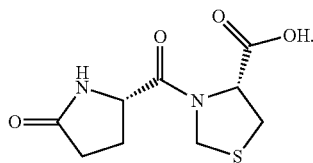 [SMILES: O=C1CC[C@@H](C(=O)N2CSC[C@H]2C(=O)O)N1]

Levamisole hydrochloride is represented by the formula:

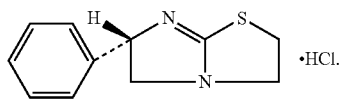

In the present invention, the immunomodulatory small molecule drug is usually a compound having a molecular weight of less than 1000, preferably less than 500. In a preferable aspect of the present invention, the immunomodulatory small molecule drug is one or more compounds selected from the group consisting of bestatin, pidotimod and levamisole hydrochloride.

As above described, the inventors have found that among a variety of cellular immunity induction promoters, a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor are particularly suitable for enhancing immune response induced by transdermal administration of the WT1 peptide antigen and/or the modified WT1 peptide antigen. Therefore, in one aspect, the cellular immunity induction promoter of the present invention is one or more substances selected from them. According to a particularly preferred aspect of the present invention, the cellular immunity induction promoter is a combination of a helper peptide and one or more selected from a TLR ligand, a cyclic dinucleotide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenaline receptor antagonist, an adrenaline receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor and a Th2 cytokine inhibitor. The induction of cellular immunity can be determined quantitatively by a variety of known methods. Any of those known method, for example, the ELISPOT method described in Examples may be used in this application.

As used herein, the non-invasive administration means administration without actively giving physical irritation and/or chemical irritation, preferably without giving physical irritation (e.g. without giving irritation by tape stripping or microneedle) to a skin.

As used herein, the term "mildly irritating condition" means a condition under which irritation to be given to the skin is lower than the irritation generally given in order to improve the skin permeability of the antigen contained in conventional vaccines, or a condition under which irritation is not given to the skin at all. In general, physical and/or chemical stimulation is given to the skin before or simultaneously with the transdermal administration of a conventional vaccine composition so that the antigen can penetrate through the skin. In a preferable aspect of this invention, examples of the mildly irritating condition include a condition of low physical irritation and a condition of low chemical irritation. The condition of low physical irritation is, for example, a condition under which transepidermal water loss (TEWL) (g/h·m$^2$) in the model animal for skin irritation evaluation is 50 or less, preferably 45 or less, more preferably 40 or less, even more preferably 35 or less, further preferably 30 or less. Since the TEWL level in non-treated skin is about 2 (g/h·m$^2$), the TEWL level before the administration of the vaccine tape preparation may be 2 (g/h·m$^2$) or more. The condition of low chemical irritation is, for example, a condition under which the thymic stromal lymphopoietin (TSLP) level (pg/mg protein) in the skin of the model animal for skin irritation evaluation is 10000 or less, preferably 9000 or less, more preferably 8000 or less, further preferably 7000 or less. Since the TSLP level is about (pg/mg protein) in non-treated skin, the TSLP level at completion of the application of the vaccine tape preparation exceeds 1 (pg/mg protein), preferably exceeds 2 (pg/mg protein), more preferably exceeds 3 (pg/mg protein). The "thymic stromal lymphopoietin (TSLP)" is a cytokine which participates in differentiation and recruitment of T cells, and can be utilized as an index of the degree of skin irritation in the present invention. Greater TSLP value means stronger skin irritation. Examples of means for attaining the condition of low physical irritation include not-conducting the conventional pre-treatment of the skin before the administration such as not conducting tape stripping or microneedle puncture before the administration. Examples of means for attaining the condition of low chemical irritation include avoiding administration of an irritating chemical ingredient such as ethanol or a surfactant at a certain amount or more. The procedure for attaining the mildly irritating condition can be determined by using a model animal for skin irritation evaluation, and the determined procedure can be applied to the subject to be treated by the vaccine tape preparation, for example, a human subject.

As used herein, the term "cancer" means a cancer associated with abnormal expression, for example, overexpression of the WT1 gene. Examples of cancer may include hematopoietic tumors and solid cancers. Examples of the hematopoietic tumors associated with abnormal expression of the WT1 gene include, but are not limited to, leukemia such as acute myelocytic leukemia, acute lymphocytic leukemia and chronic myelocytic leukemia, myelodysplastic syndrome, multiple myeloma, as well as malignant lymphoma such as non-Hodgkin's lymphoma. Examples of the solid cancers associated with abnormal expression of the WT1 gene include, but are not limited to, lung cancer, breast cancer, stomach cancer, large intestine/rectum cancer, germ cell cancer, liver cancer, skin cancer, pancreas cancer, bile duct cancer, head and neck squamous cell cancer, thyroid cancer, kidney cancer, bladder cancer, prostate cancer, ovarian cancer, uterine cancer, cervical cancer, bone soft tissue sarcoma, malignant melanoma, malignant mesothelioma, testicular germ cell tumor and malignant glioma.

As used herein, the term "abnormal expression of a gene" means that the expression level of the gene in a cell is increased or decreased remarkably, for example, by 2 times or more such as by 4 times or more, as compared with the other cells in the same tissue. The term "overexpression" means that the abnormal expression is an increase in the expression level. The expression level of a gene can be easily measured using any method well-known in the art.

As used herein, the term "subject" means any animal having the WT1 gene whose immune response can be induced by applying a cancer vaccine tape preparation to the skin at a practical stage. Typically, the subject may be a mammal such as human, mouse, rat, dog, cat, rabbit, horse, cow, sheep, pig, goat, monkey, and chimpanzee. A particularly preferable subject is human.

As used herein, the term "model animal for immunological evaluation" means a model animal for evaluating the property of a cancer vaccine tape preparation to induce immunity. Specifically, it means a model animal for evaluating the property of inducing cellular immunity. The model animal for immunological evaluation should be selected in view of compatibility between the antigen in the vaccine tape preparation to be evaluated and the MHC class 1 molecule of the animal. An animal model suitable for evaluating the property of the vaccine tape preparation to induce the cellular immunity should be used. For example, in the case of a vaccine tape preparation containing a HLA-A*24 type MHC restricted class 1 peptide, the property may be evaluated in a BALB/c mouse. In the case of a vaccine tape preparation containing a HLA-A*02 type MHC restricted peptide, the property may be evaluated in a genetically modified mouse by which immunity induction by the HLA-A*02 type MHC restricted peptide can be evaluated. In the case of a vaccine tape preparation containing other HLA type MHC restricted peptide, the property is evaluated in an animal by which immunity induction by the HLA type MHC restricted peptide can be evaluated. In the case of a vaccine tape preparation containing a protein antigen, the property is evaluated in an animal having MHC compatible with a class 1 epitope to be used to induce the immunity, among various class 1 epitopes included in the amino acid sequence of the protein antigen. In addition, in the case of a cancer vaccine tape preparation using Db126 peptide which is compatible with not only HLA-A*02 type but also MHC-H-2Db type, not only a genetically modified mouse by which immunity induction by the HLA-A*0201 type MHC restricted peptide can be evaluated, but also a C57BL/6 mouse which is an animal having MHC-H-2Db type can be used as the model mouse for immunological evaluation. When the hair of the animal is cut to ensure the place for transdermal administration, the animal should be used after it is recovered from the skin damage caused by the hair cut.

As used herein, the term "model animal for skin irritation evaluation" means a model animal for evaluating transepidermal water loss (TEWL) as an index of physical irritation of the skin, or a model animal for evaluating TSLP as an index of the skin irritation property of a cancer vaccine tape preparation. Regardless of the kind of the antigen contained in the cancer vaccine tape preparation, C57BL/6 mouse may be used as model animal for skin irritation evaluation. When the hair of the animal is cut to ensure the place for the transdermal administration, the animal should be used after it is recovered from the skin damage caused by the hair cut.

II. Cancer Vaccine Tape Preparation

It has already been revealed that WT1 peptides and/or the modified WT1 peptides are useful as cancer vaccine (e.g. Patent Document 1).

The tape preparation contains an adhesive layer comprising an adhesive and the active ingredient which is the WT1 peptide and/or the modified WT1 peptide, and a support which supports the adhesive layer, in the case of a matrix type tape preparation. In the case of a reservoir type tape preparation, the tape preparation contains a reservoir containing the active ingredient and an adhesive layer, and a support which supports the reservoir and an adhesive layer. The tape preparation, optionally, may further contain a release liner which does not expose the adhesive layer before use and can be easily peeled from the adhesive layer upon use. Hereinafter, representatively, a tape preparation will be explained in detail.

The adhesive layer of the tape preparation contains the WT1 peptide and/or the modified WT1 peptide, and the cellular immunity induction promoter. In one aspect, the adhesive layer contains the WT1 peptide and/or the modified WT1 peptide preferably in an amount of 0.01 to 40% by weight, more preferably 0.1 to 30% by weight based on the total weight of the adhesive layer. In one aspect, the adhesive layer contains the cellular immunity induction promoter preferably in an amount of 0.001 to 30% by weight, more preferably 0.01 to 20% by weight based on the total weight of the adhesive layer.

An adhesive which is to form the adhesive layer of the tape preparation of the present invention is not particularly limited, and examples thereof include acrylic adhesives consisting of an acrylic polymer; rubber adhesives comprising a rubber elastomer such as a styrene-diene-styrene block copolymer (e.g. styrene-isoprene-styrene block copolymer, styrene-butadiene-styrene block copolymer etc.), polyisoprene, polyisobutylene, butyl rubber, polybutadiene and the like; silicone adhesives such as silicone rubber, dimethylsiloxane base, diphenylsiloxane base and the like; vinyl ether adhesives such as polyvinyl methyl ether, polyvinyl ethyl ether, polyvinyl isobutyl ether and the like; vinyl ester adhesives such as vinyl acetate-ethylene copolymer and the like; and polyester adhesives consisting of a carboxylic acid component such as dimethyl terephthalate, dimethyl isophthalate, dimethyl phthalate, and a polyhydric alcohol component such as ethylene glycol. A particularly preferable adhesive is an acrylic adhesive, a rubber adhesive, and a silicone adhesive. These adhesives are contained in the adhesive layer preferably in an amount of 10 to 90% by weight, more preferably 20 to 80% by weight, as a solid matter thereof, based on the total weight of the adhesive layer.

Examples of the acrylic adhesive include an acrylic acid ester adhesive containing, as a main component, a polymer comprising (meth)acrylic acid C2-C18 alkyl ester as a first monomer. Examples of the (meth)acrylic acid alkyl ester (first monomer) include (meth)acrylic acid alkyl esters in which an alkyl group is a straight, branched or cyclic alkyl group having 1 to 18 carbon atoms (e.g. methyl, ethyl, propyl, butyl, pentyl, hexyl, cyclohexyl, heptyl, octyl, 2-ethylhexyl, nonyl, decyl, undecyl, dodecyl, tridecyl etc.). Preferred are (meth)acrylic acid alkyl esters in which an alkyl group is a straight, branched or cyclic alkyl group having 4 to 18 carbon atoms (e.g. butyl, pentyl, hexyl, cyclohexyl, heptyl, octyl, 2-ethylhexyl, nonyl, decyl, undecyl, dodecyl, tridecyl etc.). Further, since use of a monomer component which lowers the glass transition temperature of a polymer is suitable in order to impart adhesiveness at a room temperature, (meth)acrylic acid alkyl esters in which an alkyl group is a straight, branched or cyclic alkyl group having 4 to 8 carbon atoms (e.g. butyl, pentyl, hexyl, cyclohexyl, heptyl, octyl, 2-ethylhexyl etc., preferably butyl, 2-ethylhexyl, and cyclohexyl, particularly preferably 2-ethylhexyl) are more preferable. Specifically, butyl acrylate, 2-ethylhexyl acrylate, 2-ethylhexyl methacrylate, cyclohexyl acrylate, cyclohexyl methacrylate and the like are more preferable and, among them, 2-ethylhexyl acrylate is most preferable. These (meth)acrylic acid alkyl esters (first monomer component) can be used alone, or can be used by combining two or more thereof.

In addition, the acrylic adhesive may contain a second monomer copolymerizable with the (meth)acrylic acid alkyl ester, and examples of the second monomer include monomers having a functional group which can become a crosslinking point upon use of a crosslinking agent. Examples of the functional group which can participate in a crosslinking reaction include a hydroxy group, a carboxyl group, a vinyl group and the like, and a hydroxy group and a carboxyl group are preferable. Specific examples of the monomer (second monomer component) include (meth)acrylic acid hydroxyethyl ester, (meth)acrylic acid hydroxypropyl ester, N-hydroxyalkyl(meth)acrylamide, (meth)acrylic acid, itaconic acid, maleic acid, maleic anhydride, mesaconic acid, citraconic acid, glutaconic acid and the like. Among them, from the viewpoint of easy availability, acrylic acid, methacrylic acid, and acrylic acid hydroxyethyl ester (particularly, 2-hydroxyethyl acrylate) are preferable, and acrylic acid is most preferable. These monomers (second monomer component) can be used alone, or can be used by combining two or more thereof.

Further, the acrylic adhesive may optionally contain a third monomer in addition to the second monomer. Examples of the third monomer (third monomer component) include vinyl esters such as vinyl acetate, vinyl propionate and the like; vinyl ethers such as methyl vinyl ether, ethyl vinyl ether and the like; vinyl amides such as N-vinyl-2-pyrrolidone, N-vinylcaprolactam and the like; (meth)acrylic acid alkoxy esters such as (meth)acrylic acid methoxyethyl ester, (meth)acrylic acid ethoxyethyl ester, (meth)acrylic acid tetrahydrofurfuryl ester and the like; hydroxy group-containing monomers (since this is used as a third monomer component, it is not a crosslinking point) such as hydroxypropyl (meth)acrylate, α-hydroxymethyl acrylate and the like; (meth)acrylic acid derivatives having an amide group such as (meth)acrylamide, dimethyl(meth)acrylamide, N-butyl(meth)acrylamide, N-methylol(meth)acrylamide and the like; (meth)acrylic acid aminoalkyl esters such as (meth)acrylic acid aminoethyl ester, (meth)acrylic acid dimethylaminoethyl ester, (meth)acrylic acid t-butylaminoethyl ester and the like; (meth)acrylic acid alkoxyalkylene glycol esters such as (meth)acrylic acid methoxyethylene glycol ester, (meth)acrylic acid methoxydiethylene glycol ester, (meth)acrylic acid methoxypolyethylene glycol ester, (meth)acrylic acid methoxypolypropylene glycol ester and the like; (meth)acrylonitriles; monomers having sulfonic acid such as styrenesulfonic acid, allylsulfonic acid, sulfopropyl(meth)acrylate, (meth)acryloyloxynaphthalenesulfonic acid, acrylamidemethylsulfonic acid and the like; and vinyl-group-containing monomers such as vinylpiperidone, vinylpyrimidine, vinylpiperazine, vinylpyrrole, vinylimidazole, vinyloxazole, vinylmorpholine and the like. Among them, vinyl esters and vinyl amides are preferable, vinyl acetate is preferable as vinyl esters, and N-vinyl-2-pyrrolidone is preferable as vinyl amides. These monomers (third monomer component) can be used alone, or can be used by combining two or more kinds thereof.

When the acrylic adhesive is a copolymer of a (meth)acrylic acid alkyl ester (first monomer component) and a vinyl monomer having a functional group which can participate in a crosslinking reaction (second monomer component), the (meth)acrylic acid alkyl ester and the vinyl monomer having a functional group which can participate in a crosslinking reaction are copolymerized by blending the components at a weight ratio of (meth)acrylic acid alkyl ester:vinyl monomer having a functional group which can participate in a crosslinking reaction of preferably 99 to 85:1 to 15, more preferably 99 to 90:1 to 10.

Further, when the acrylic adhesive is a copolymer of a (meth)acrylic acid alkyl ester (first monomer component), a vinyl monomer having a functional group which can participate in a crosslinking reaction (second monomer component), and a monomer other than them (third monomer component), the (meth)acrylic acid alkyl ester, the vinyl monomer having a functional group which can participate in a crosslinking reaction, and the monomer other than them are copolymerized by blending the components at a weight ratio of (meth)acrylic acid alkyl ester:vinyl monomer having a functional group which can participate in a crosslinking reaction:monomer other than them of preferably 40 to 94:1 to 15:5 to 50, more preferably 50 to 89:1 to 10:10 to 40.

The components may be polymerized by a known method. For example, the monomers in a solvent such as ethyl acetate may be reacted in the presence of a polymerization initiator (e.g. benzoyl peroxide, azobisisobutyronitrile etc.) at 50 to 70° C. for 5 to 48 hours.

Particularly preferable acrylic adhesives in the present invention are, for example, a copolymer of acrylic acid 2-ethylhexyl ester/acrylic acid/N-vinyl-2-pyrrolidone, a copolymer of acrylic acid 2-ethylhexyl ester/N-(2-hydroxyethyl)acrylamide/N-vinyl-2-pyrrolidone, a copolymer of acrylic acid 2-ethylhexyl ester/acrylic acid 2-hydroxyethyl ester/vinyl acetate, and a copolymer of acrylic acid 2-ethylhexyl ester/acrylic acid, and more preferably, a copolymer of acrylic acid 2-ethylhexyl ester/acrylic acid/N-vinyl-2-pyrrolidone.

Optionally, these acrylic adhesives may be subjected to physical crosslinking treatment by ultraviolet irradiation, or radiation irradiation such as electron beam irradiation, or chemical crosslinking treatment using various crosslinking agents such as an isocyanate compound such as trifunctional isocyanate, organic peroxide, organic metal salt, metal alcoholate, metal chelate compound, polyfunctional compound (polyfunctional external crosslinking agent, a monomer for polyfunctional internal crosslinking such as diacrylate and dimethacrylate).

Examples of the rubber adhesive include rubber adhesives in which a rubber elastomer such as polyisobutylene/polybutene elastomer, styrene/diene/styrene block copolymer, styrene/butadiene elastomer, nitrile elastomer, chloroprene elastomer, vinylpyridine elastomer, polyisobutylene elastomer, butyl elastomer, or isoprene/isobutylene elastomer is blended. Among them, in view of solubility of the peptide and the cellular immunity induction promoter in the adhesive and the skin adhesiveness, polyisobutylene (PIB), styrene/diene/styrene block copolymer (e.g. styrene/butadiene/styrene block copolymer (SBS), styrene/isoprene/styrene block copolymer (SIS) etc.) and the like are preferably used. A mixture of two or more of those adhesives may also be used.

Further, in order to achieve a suitable adhesive force and drug solubility of the rubber adhesive, the rubber adhesive may be a mixture of two or more rubber elastomers of the same or different monomer components each having different average molecular weights. For example, with respect to polyisobutylene, a mixture of polyisobutylene of high molecular weight having an average molecular weight of 150,000 to 5,500,000, polyisobutylene of medium molecular weight having an average molecular weight of 10,000 to 150,000 and/or polyisobutylene of low molecular weight having an average molecular weight of 500 to 4,000 is preferable. In this case, it is preferable to blend polyisobutylenes of high molecular weight, medium molecular weight and low molecular weight at a weight ratio of high molecular weight:medium molecular weight:low molecular weight=10 to 80, preferably 20 to 70:0 to 90, preferably 10 to 80:0 to 80, preferably 10 to 60.

As used herein, the average molecular weight means the viscosity average molecular weight calculated from the viscosity expression of Flory, and is obtained by calculating the Staudinger index ($J_0$) from the flow time of the capillary 1 of a Ubbelohde viscometer at 20° C. by the Schulz-Blaschke expression, and using this $J_0$ value with the following expression.

$$J_0 = \eta_{sp}/c(1+0.31\eta_{sp}) \text{ (Schulz-Blaschke equation)}$$

$$\eta_{sp} = t/t_0 - 1 \quad \text{(Formula)}$$

t: Flow time of solution (according to Hagenbach-couette correction formula)

$t_0$: Flow time of solvent (according to Hagenbach-couette correction formula)

c: Concentration of solution (g/cm$^3$)

$$J_0 = 3.06 \times 10^{-2} \overline{Mv}^{0.65}$$

$\overline{Mv}$: Viscosity average molecular weight

In order to impart suitable adhesiveness, for example, a tackifier such as a rosin resin, a polyterpene resin, a coumarone-indene resin, a petroleum resin, a terpene-phenol resin, a xylene resin, an alicyclic saturated hydrocarbon resin or the like may be blended in the rubber adhesive. One, two or more kinds of tackifiers can be blended in an amount of 50% by weight or less, preferably 5 to 40% by weight based on the total weight of the rubber adhesive.

Examples of the silicone adhesive include silicone adhesives consisting of polyorganosiloxane adhesive, polydimethylsiloxane adhesive, and polydimethyldiphenyl-siloxane adhesive. Inter alia, a commercially available silicone adhesive such as BIO PSA from Dow Corning Corporation is preferably used.

The support which supports the adhesive layer is not particularly limited, and a support that is substantially impervious to the peptide and the cellular immunity induction promoter so that the peptide, the cellular immunity induction promoter, additives or the like contained in the adhesive layer will not pass through the support and leaked from the rear surface.

As the support, for example, a single film of polyester, polyamide, poly(vinylidene chloride), polyethylene, polypropylene, poly(vinyl chloride), ethylene-ethyl acrylate copolymer, polytetrafluoroethylene, ionomer resin, metal foil or the like, or a laminate film of them can be used. Among them, in order to make adhesiveness (anchorability) between the support and the adhesive layer good, it is preferable that the support is a laminate film of a nonporous plastic film and a porous film made of the aforementioned material. In this case, it is desirable that the adhesive layer is formed on the porous film side. As such a porous film, a porous film which improves anchorability with the adhesive layer is adopted, and specific examples thereof include a paper sheet, a woven fabric, a non-woven fabric, a knitted fabric, a sheet which has been mechanically perforation-treated, and the like. Among them, from the viewpoint of handling property and the like, particularly, a paper sheet, a woven fabric and a non-woven fabric are preferable. As the porous film, in view of improvement in anchorability, softness and sticking operability of a tape preparation and the like, a porous film having a thickness in the range of 1 to 200 μm is adopted. In addition, when a woven fabric or a non-woven fabric is used as the porous film, the weight per unit area is preferably 5 to 30 g/m$^2$, more preferably 6 to 15 g/m$^2$.

Examples of most suitable supports include a laminate film of a polyester film (preferably, polyethylene terephthalate film) having a thickness of 1.5 to 6 μm, and a non-woven fabric made of polyester (preferably, polyethylene terephthalate) having a weight per unit area of 6 to 15 g/m$^2$.

In the tape preparation of the present invention, in order to protect the surface of the adhesive layer until use, it is desirable that a release liner is laminated on the adhesive surface. The release liner is not particularly limited as far as it is treated so that it has the releasing property and it can be released with a sufficiently small peeling force. For example, a film of polyester, poly(vinyl chloride), poly(vinylidene chloride), polyethylene terephthalate or the like, paper such as pure paper, glassine paper and the like, or a laminate film of pure paper or glassine paper and polyolefin may be treated by coating a silicone resin, a fluorine resin or the like on the surface to be contacted with the adhesive layer and is used as the release liner. The thickness of the release liner is preferably 10 to 200 μm, more preferably 25 to 100 μm. As the release liner, polyester layer, particularly, polyethylene terephthalate layer is preferable in view of the barrier property and the cost. Further, in this case, in terms of handling property, a release liner having a thickness of around 25 to 100 μm is preferable.

It is preferable that the tape preparation of the present invention is applied to a subject under the mildly irritating condition. Administration under the mildly irritating condition can be attained, for example, by (i) applying the tape preparation of the present invention to the subject under such a condition that transepidermal water loss (TEWL) (g/h·m$^2$) evaluated in a model animal for skin irritation evaluation is 50 or less, or (ii) applying to a subject the tape preparation providing the cutaneous TSLP level (pg/mg protein) of 10000 or less evaluated in a model animal for skin irritation evaluation.

In addition, the cellular immunity induction promoting effect of the tape preparation of the present invention can be improved by supplementing an additional cellular immunity induction promoter that may be a pharmacologically acceptable acid or a pharmacologically acceptable salt thereof.

As used herein, the "pharmacologically acceptable acid" which can be contained in the tape preparation of the present invention means an acid which has no harmful effect on a subject to which the tape preparation is applied, and does not impair the pharmacological activity of the ingredients in the tape preparation. In a preferable aspect of the present invention, the pharmacologically acceptable acid is an organic acid, more preferably an organic compound containing carboxyl group or an organic compound containing sulfo group, more preferably saturated or unsaturated straight or branched fatty acid in which the saturated straight chain part has 8 to 20 carbon atoms, lactic acid, malic acid, salicylic acid, maleic acid, citric acid, or an organic compound containing sulfo group, more preferably saturated or unsaturated straight or branched fatty acid in which the saturated straight chain part has 8 to 16 carbon atoms, lactic acid, malic acid, salicylic acid, maleic acid, citric acid, or an organic compound containing sulfo group, further preferably fatty acid selected from the group consisting of decanoic acid, lauric acid, myristic acid, isostearic acid and oleic acid, or lactic acid, salicylic acid, citric acid or methanesulfonic acid.

As used herein, a "pharmacologically acceptable salt" which can be contained in the tape preparation of the present invention means a salt which has no harmful effect on a subject to be applied with the tape preparation, and does not impair the pharmacological activity of the ingredients in the tape preparation. Examples of pharmacologically acceptable salts include inorganic acid salts (e.g. hydrochloric acid salt and phosphoric acid salt), organic acid salts (e.g. acetic acid salt, phthalic acid salt, and TFA salt), metal salts (alkali metal salts (e.g. sodium salt and potassium salt), alkaline earth metal salts (e.g. calcium salt and magnesium salt), aluminum salt etc.), and amine salts (triethylamine salt, benzylamine salt, diethanolamine salt, t-butylamine salt, dicyclohexylamine salt, arginine salt, dimethylammonium salt, ammonium salt etc.), but are not limited to them.

In addition, the tape preparation of the present invention may contain an additive, if necessary. The additive is selected from, for example, isotonizing agents, antiseptics/germicides, antioxidants, resolvents, solubilizers, suspending agents, fillers, pH adjusting agents, stabilizers, skin permeability enhancers, release rate controlling agents, coloring agents, plasticizers, crosslinking agents, adhesives and the like, or a combination of two or more kinds of them, depending on the compatibility with the main ingredient of the base, the WT1 peptide and/or the modified WT1 peptide and the cellular immunity induction promoter, intended administration regimen and the like.

As used herein, the term "skin permeability enhancer" means any substance which can improve an efficiency of permeation of a transdermally administered antigen through the skin, as compared with the efficiency obtained without the substance. The skin permeability enhancer is not particularly limited as far as it is liquid at room temperature (25° C.), that is, has fluidity at that temperature and has an absorption promoting effect. When the skin permeability enhancer is a mixture of two or more substances, the mixture is liquid at room temperature (25° C.) and has an absorption promoting effect. The skin permeability enhancer may be an organic liquid and preferably, a hydrophobic liquid in view of their compatibility with the adhesive layer.

Examples of skin permeability enhancers include higher alcohols such as oleyl alcohol, octyldodecanol and the like; polyhydric alcohols such as glycerin, ethylene glycol, polypropylene glycol and the like; higher fatty acids such as oleic acid, caprylic acid and the like; fatty acid esters such as isopropyl myristate, isopropyl palmitate, ethyl oleate and the like; polybasic acid esters such as diethyl sebacate, diisopropyl adipate and the like; polyhydric alcohol fatty acid esters such as diglyceryl triisostearate, monooleic acid sorbitan, dicaprylic acid propylene glycol, monolauric acid polyethylene glycol, tetraoleic acid polyoxyethylene sorbit and the like; polyoxyethylene alkyl ethers such as polyoxyethylene lauryl ether and the like; hydrocarbons such as squalane, liquid paraffin and the like; plant oils such as olive oil, castor oil and the like; silicone oils; pyrrolidones such as N-methylpyrrolidone, N-dodecylpyrrolidone and the like; sulfoxides such as decylmethyl sulfoxide and the like, and these can be used alone, or can be used by mixing two or more kinds thereof.

When a rubber-based adhesive or an acrylic adhesive is used, a second skin permeability enhancer can be used. Specific examples of the second skin permeability enhancer include, but are not limited to, polyvinylpyrrolidone, crospovidone, polypropylene glycol, polyvinyl alcohol, carboxyvinyl polymers, hydroxypropyl cellulose, and mixtures thereof. According to a preferred aspect, the second skin permeability enhancer of the present invention is polyvinylpyrrolidone, crospovidone, and/or polypropylene glycol.

From the viewpoint of enhancing the skin permeability of the WT1 peptide and/or the modified WT1 peptide, examples of the skin permeability enhancer that can be preferably used include higher alcohols; more specifically, higher alcohols having 8 to 18 carbon atoms (preferably 8 to 14 carbon atoms), and fatty acid esters; more specifically, fatty acid esters between a fatty acid having 8 to 18 carbon atoms (preferably 12 to 16 carbon atoms) and a monohydric alcohol having 1 to 18 carbon atoms, and polyhydric alcohol fatty acid esters; and particularly preferably fatty acid esters, particularly isopropyl myristate, isopropyl palmitate, or diethyl sebacate. The amount of such a skin permeability enhancer is preferably 0.1% by weight to 70% by weight, more preferably 1% by weight to 65% by weight, and even more preferably 5% by weight to 60% by weight, relative to the total weight of the adhesive layer. When the proportion of the skin permeability enhancer is 0.1% by weight or more, a high transdermal absorption accelerating effect can be obtained. When the proportion is 70% by weight or less, it is advantageous because high transdermal absorbability can be obtained while a decrease in the adhesive force and cohesive force of the adhesive layer as a whole is suppressed.

The therapeutically effective amount of the WT1 peptide and/or the modified WT1 peptide may widely vary depending on severity of the disease, age and relative health of the subject and other known factors. In general, satisfactory result may be obtained at a one day dose of about 0.1 μg to 1 g/kg body weight. The cellular immunity induction promoter is administered simultaneously with the WT1 peptide and/or the modified WT1 peptide or sequentially, and preferably, it is administered simultaneously with the peptide. The effective amount of the cellular immunity induction promoter may widely vary depending on the kind of cellular immunity induction promoter to be used, the presence or absence of other cellular immunity induction promoter and the like, and satisfactory result is obtained at a one day dose of about 0.01 μg to 1 g/kg body weight. The one day dose may be administered in a single dose or in several divided portions at several times such as two times or more, for example, two, three, four or five times. The tape preparation may be applied continuously for a period of between 1 minute and 7 days per one administration. The administration interval is appropriately selected from once every day to once per year (e.g. once per one day, once per 2 days, once per 3 days, once per one week, once per 2 weeks, once per one month, once per 3 months, once per 6 months, once per one year) and longer depending on the state of the patient, severity of the cancer, whether it is for therapeutic purpose or preventive purpose, or the like. Generally, for the purpose of treating a patient actually having a severe cancer, the WT1 peptide and/or the modified WT1 peptide are administered at a higher frequency and a higher dose, while for the preventive purpose for a patient having no cancer, the WT1 peptide and/or the modified WT1 peptide are administered at a lower frequency and a lower dose.

In the present invention, physical irritation means any physical irritation which gives damage to corneum, including scratch and scraping. For example, operation of tape stripping which removes corneum with an adhesive tape or the like, operation of giving damage to the skin with a cutter, and operation using a microneedle such as perforation in corneum are also included in the physical irritation.

Transepidermal water loss means the amount (g) of water which is transpired from 1 $m^2$ of keratin per one hour. The transepidermal water loss can be easily measured in a short time with a water loss measuring device, and is widely used as an index for evaluating the damage degree of the skin. Also in the present invention, the transepidermal water loss can be used as an index of the physical irritation level.

TSLP (Thymic stromal lymphopoietin) is one of IL-7-like cytokines which is produced by keratinocyte of skin, thymus, and mucosal epithelial cells, and is known to be involved in the maturation of dendritic cells, and the differentiation of T cells. In the present invention, the TSLP level can be used as an index of the chemical irritation level which is irritation derived from a drug.

The present invention will be explained in more detail and specifically below by way of Examples. The present invention is not limited to the Examples.

EXAMPLES

Tape Preparation

Adhesives for tape preparations were prepared.
(Polymerization of Acrylic Adhesive A)
Under an inert gas atmosphere, 75 parts of 2-ethylhexyl acrylate, 22 parts of N-vinyl-2-pyrrolidone, 3 parts of acrylic acid and 0.2 part of azobisisobutyronitrile were solution polymerized at 60° C. in ethyl acetate to obtain acrylic adhesive A solution.
(Polymerization of Acrylic Adhesive B)
Under an inert gas atmosphere, 70 parts of 2-ethylhexyl acrylate, 25 parts of N-vinyl-2-pyrrolidone, 5 parts of N-(2-hydroxyethyl)acrylamide and 0.2 part of azobisisobutyronitrile were solution polymerized at 60° C. in ethyl acetate to obtain acrylic adhesive B solution.
(Preparation of PIB Rubber Adhesive)
24 parts of polyisobutylene (Oppanol B200, manufactured by BASF), 36 parts of polyisobutylene. (Oppanol B12, manufactured by BASF) and 40 parts of an alicyclic petroleum resin (Arkon P-100, manufactured by Arakawa Chemical Industries, Ltd.) were dissolved in toluene to obtain PIB rubber adhesive solution.

(Preparation of SIS Adhesive A)
60 parts of a styrene-isoprene-styrene block copolymer (SIS5002, manufactured by JSR Corporation), and 40 parts of an alicyclic petroleum resin (Arkon P-100, manufactured by Arakawa Chemical Industries, Ltd.) were dissolved in toluene to obtain SIS adhesive A solution.
(Preparation of SIS-PIB Adhesive A)
30 parts of a styrene-isoprene-styrene block copolymer (SIS5002, manufactured by JSR Corporation), 30 parts of polyisobutylene (Oppanol B100, manufactured by BASF) and 40 parts of an alicyclic petroleum resin (Arkon P-100, manufactured by Arakawa Chemical Industries, Ltd.) were dissolved in toluene to obtain SIS-PIB adhesive A solution.

Tape preparations having the ingredients shown in the following Table 1 were manufactured. Specifically, Db126 antigen peptide, a cellular immunity induction promoter and, optionally, a skin permeability enhancer and/or a pharmacologically acceptable acid and/or an additive, an adhesive solution and an organic solvent (ethyl acetate, etc.) in the amounts described in Table 1 were blended, kneaded, and spread on a release liner so that the thickness of the layer after drying became about 80 µm, the organic solvent was removed by drying, and a support was stuck to the layer to prepare a tape preparation. The adhesive solution was blended so that the total amount of the ingredients and the adhesive after drying organic solvent became 100 parts by weight. Polyethylene terephthalate (PET) film (thickness 25 µm) was used as the support. Polyethylene terephthalate (PET) sheet (thickness 75 µm) treated with silicone was used as release liner. Thus obtained tape preparation was cut to give a piece of 0.7 $cm^2$, and was adopted to the immunization test. The release liner was peeled just before the application of the tape preparation.

Acetate of Db126 peptide, Peptide-25 (Pep25), PADRE (universal helper peptide), $WT1_{35}$ ($hWT1_{35}$ helper peptide) and $WT1_{332}$ ($WT1_{332-34}7$ helper peptide) were chemically synthesized and were purified by HPLC before use. Imiquimod (IMQ) was purchased from Tokyo Chemical Industry Co., Ltd. Cyclic di-GMP (c-di-GMP) and cyclic di-AMP (c-di-AMP) were purchased from Biolog Life Science Institute GmbH. *Pantoea* bacterium-derived lipopolysaccharide was a product manufactured by Institute of Applied Technology for Innate Immunity; glucopyranosyl lipid was a product manufactured by InvivoGen, Inc. (MPLAs); sodium hyaluronate was a product of Kikkoman Biochemifa Co. (Microhyaluronic acid FCH); ODN1826 was a product manufactured by InvivoGen, Inc.; pidotimod was a product manufactured by Santa Cruz Biotechnology, Inc., bestatin was a product manufactured by Wako Pure Chemical Industries, Ltd., levamisole hydrochloride was a product manufactured by MP Biomedicals, LLC; etodolac was a product manufactured by Wako Pure Chemical Industries, Ltd.; and loxoprofen Na was a product manufactured by Yoshindo, Inc.

Clofibrate: manufactured by LKT Laboratories, Inc., quercetin: manufactured by Cayman Chemical Co., GW627368X: manufactured by Cayman Chemical Co., sulprostone: manufactured by Cayman Chemical Co., tranilast: manufactured by Wako Pure Chemical Industries, Ltd., immepip (immepip dihydrobromide): manufactured by Tocris Bioscience, azelastine (azelastine hydrochloride): manufactured by LKT Laboratories, Inc., yohimbine (yohimbine hydrochloride): manufactured by Wako Pure Chemical Industries, Ltd., sumatriptan: manufactured by Myung In Pharm. Co., Ltd., oxybutynin (oxybutynin hydrochloride): manufactured by Sigma-Aldrich, tamsulosin (tamsulosin hydrochloride): manufactured by Cipla, loperamide (loperamide hydrochloride):manufacturedbyWako Pure Chemical Industries, Ltd., melatonin: manufactured by LKT Laboratories, Inc., and L-AP4 (L-2-amino-4-phsophonobutyric acid): manufactured by Wako Pure Chemical Industries, Ltd., were used.

Mouse Immunization Test 1 (Tape Preparation)

Mouse immunization test was performed with the tape preparations using a model animal for immunological evaluation. Evaluation of the immunity induction level was performed by the ELISPOT method. Specifically, the hair of the back of the mouse was cut. The mouse was kept until it recovered from the skin damage due to the hair cutting. After that, a sample was applied to the back of the mouse for the predetermined time, and then removed. Then, the mouse was kept for predetermined days and the level of the antigen-specific cellular immunity was evaluated. After predetermined days from the application of the sample, the spleen was isolated and a spleen cell suspension was prepared. Spleen cells ($3\times10^6$ cells/well) and the antigen peptide (100 μM) together with the culturing medium were placed into a well of an ELISPOT plate on which an anti-mouse IFN-γ antibody had been immobilized. The plate was cultured for 20 hours under the condition of 37° C. and 5% $CO_2$. The number of the spots representing IFN-γ-producing cells (spot number/$3\times10^6$ cells) was evaluated by the ELISPOT method.

The amount of administration of the tape preparation was set to 0.7 $cm^2$ as described above, the number of administrations was (24 hr/week)×once, and extraction of the spleen was carried out 6 days after the administration. The mouse used for the experiment was a genetically modified mouse by which cellular immunity induction caused by HLA-A*0201 type MHC-restricted peptide can be evaluated.

In Example 8, administration was carried out on skin that was injured with a microcutter (MICRO FEATHER No. 7330G, manufactured by Feather Safety Razor Co., Ltd.).

For some tape preparations, the TSLP level in the skin of the mouse after administration, the transepidermal water loss of the mouse before administration, and the skin permeability of Db126 peptide and imiquimod were measured. The mouse used for the evaluation of the TSLP level, the transepidermal water loss, and skin permeability was C57BL/6 mouse.

(Method of Measuring TSLP Level)

The TSLP level was evaluated using C57BL/6 mouse as a model animal for skin irritation evaluation. The sample was applied to the model mouse for skin irritation evaluation under the same condition applied in the Mouse immunization test 1. When the application of the sample was completed, the skin of the back of the mouse was isolated, and the skin was ground using a homogenizer (Physcotron, Microtec Co., Ltd.) in an extraction solvent (PBS solution containing a protease inhibitor (Protease Inhibitor Cocktail for general use, manufactured by Sigma-Aldrich) and 10 μM indomethacin (manufactured by Wako Pure Chemical Industries, Ltd.)). The ground skin was centrifuged at 4° C. and 9000 g for 10 minutes, and the supernatant was recovered. The TSLP amount in the supernatant was measured by ELISA (Mouse TSLP Quantikine ELISA Kit, manufactured by R&D Systems). In addition, the total protein amount in the supernatant was measured by the BCA method (Pierce BCA Protein Assay Kit, manufactured by Thermo Fisher Scientific K.K.), and the TSLP amount was divided by the total protein amount for standardization.

(Measurement of Transepidermal Water Loss)

Measurement was performed using a portable type switching chamber water loss measuring device (VAPO SCAN AS-VT100RS, manufactured by Asahibiomed Co., Ltd.). The device was contacted to the skin of the mouse for around 5 to 15 seconds to determine the value. The TEWL (g/h·$m^2$) was measured 10 minutes after applying the pre-treatment.

(Mouse Skin Permeability Test)

The skin permeability of Db126 peptide and imiquimod was determined by using a Franz type diffusion cell. The hair of the back of the mouse was previously cut. A piece of the skin was isolated from the back of the mouse and was mounted in the Franz type diffusion cell (application area 4.91 $cm^2$) in which phosphate buffer (pH 7.4 isotonic buffer) at 37° C. was circulated. A 0.7 $cm^2$ preparation was stuck on the mounted skin, and sample in the cell was collected after 24 hours. The collected sample was subjected to high performance liquid chromatograph-tandem mass spectrometer, and the amount of Db126 peptide which permeated through the skin after 24 hours (Db126 peptide permeated amount, μg/$cm^2$/24 hr) and the amount of imiquimod (imiquimod permeated amount, μg/$cm^2$/24 hr) were calculated from a calibration curve which had been determined in advance.

The results of the immunization test, TSLP level and transepidermal water loss are shown in the following Table 1. Also, the measurement results of skin permeability are presented in Tables 2 and 3.

In Vivo CTL Assay

Seven days after final immunization, the spleen cells (target cell or control cell) were transplanted according to the following procedure, and then, the spleen was isolated after 18 hours. The % Specific Lysis was obtained by performing the FACS measurement.

Procedure 1. Collection of Spleen Cells of Naïve Mouse

Naive mouse that is the same kind mouse as that used in the immunization test was used. Spleen was isolated from the naïve mouse and mashed using a glass slide in a petri dish containing RPMI1640 medium. The mashed spleen was put into a 50 mL tube and centrifuged at 10° C. and 1100 rpm for 5 minutes. The supernatant was discarded. 20 mL of Lysis Buffer was added to the tube, followed by incubation at room temperature for 5 minutes. 20 mL of the medium was added to the tube and the tube was then centrifuged. The medium was added to the tube and the resultant was passed through a cell strainer to give spleen cell suspension.

Procedure 2. Labeling of the Spleen Cells with the Antigen

The spleen cells prepared in Procedure 1 were centrifuged at 10° C. and 1100 rpm for 5 minutes, the supernatant was discarded, and HBSS buffer was added to give cell suspension of $2\times10^7$ cells/mL. The cell suspension was dispensed into two 50 mL tubes, 100 μM of the antigen solution (the antigen was the same antigen used in the immunization test) was added to one of the tubes containing the cell solution so that the final concentration became 10 μM, to obtain a target cell. The cell in another tube was adopted as control. The cells in both tubes were incubated at 37° C. for 1 hour, centrifuged, the supernatant was discarded, and a medium was added.

Procedure 3. Labeling of the Spleen Cells with CFSE

The cell labelled with the antigen according to Procedure 2 was centrifuged, and 0.1% BSA-PBS was added to $1\times10^7$ cells/mL. To the target cell suspension was added 5 mM CFSE solution to give the final concentration of 10 μM, and to the control cell suspension was added 5 mM CFSE solution to give the final concentration of 1 μM, and the mixture was vortexed, followed by incubation at 37° C. for 10 minutes. Thereafter, centrifugation was performed, the supernatant was discarded, and the medium was added.

Procedure 4. Transplantation of Spleen Cell

The cell labelled with CFSE according to Procedure 3 was centrifuged, the supernatant was discarded, and HBSS buffer was added to the cells to give cell suspension of $5\times10^7$ cells/mL. Equal amounts of the target cell suspension and the control cell suspension were mixed, and 200 μL aliquot of the mixture was introduced into each immunized mouse via orbital veins (transplanted cell number: $1\times10^7$ cells/animal).

Procedure 5. Preparation of Spleen Cell of the Immunized Mouse and Measurement of FACS Eighteen hours after the transplantation of the spleen cells, spleen of the mouse was isolated, and spleen cell suspension was prepared in the same manner as in Procedure 1. Thereafter, CFSE-positive cells were detected by FACS, and the ratio between CFSE high cells (target cells) and CFSE low cells (control cells) was obtained. The cytotoxic activity was calculated by the formula shown below. The obtained value can be used as an index showing the ability of the antigen specific killer cells induced by the immunization with the vaccine tape preparation to attack specifically the cells that present the antigen in the living body. It was confirmed that the tape preparation of the present invention can induce strong antigen-specific cellular immunity.

$$r = (\% \text{ CFSE low cells})/(\% \text{ CFSE high cells})$$

$$\% \text{ Specific Lysis} = (1 - (r_{non\_immunized}/r_{immunized}))\times 100$$

TABLE 1

| | Composition | | | | | | TSLP | | | Results of immunization (ELISPOT average number of spots) | % Specific Lysis (In vivo CTL assay) |
|---|---|---|---|---|---|---|---|---|---|---|---|
| | Base (Adhesive) | Antigen peptide | Cellular immunity induction promoter | Skin permeability enhancer | Acid | Additive (chemical irritation) | (pg/mg protein) | Physical irritation | TEWL (g/hm²) | | |
| Comparative example 1 | PIB rubber adhesive | Db126 (10) | None | None | IPM (36) | None | None | None | None | 12 | 3 | |
| Comparative example 2 | PIB rubber adhesive | Db126 (10) | None | None | IPM (27) | MA (9) | None | None | None | 12 | 10 | |
| Example 1 | PIB rubber adhesive | Db126 (10) | IMQ (1) | None | IPM (35.6) | None | None | None | None | 12 | 25 | |
| Example 2 | PIB rubber adhesive | Db126 (10) | None | PEP (1) | IPM (35.6) | None | None | None | None | 12 | 11 | |
| Example 3 | PIB rubber adhesive | Db126 (10) | IMQ (1) | PEP (1) | IPM (35.2) | None | None | None | None | 10 | 40 | |
| Example 4 | PIB rubber adhesive | Db126 (10) | None | PEP (1) | IPM (25.8) | MA (8.6) | None | None | None | 12 | 18 | |
| Example 5 | PIB rubber adhesive | Db126 (10) | IMQ (1) | PEP (1) | IPM (25.8) | MA (8.6) | None | 48 | None | 10 | 406 | |
| Example 6 | PIB rubber adhesive | Db126 (10) | IMQ (1) | PEP (1) | IPM (25.2) | MA (8.4) | BL-4.2 (4) | 180 | None | 10 | 70 | |
| Example 7 | PIB rubber adhesive | Db126 (10) | IMQ (1) | PEP (1) | IPM (25.8) | MA (8.6) | None | None | None | 10 | 584 | 35 |
| Example 8 | PIB rubber adhesive | Db126 (10) | IMQ (3) | WT1$_{35}$ (1) | IPM (25.8) | MA (8.6) | None | None | None | 10 | 1113 | 55 |
| Example 9 | PIB rubber adhesive | Db126 (10) | IMQ (3) | WT1$_{35}$ (1) | IPM (25.8) | MA (8.6) | None | T/S10 | 58 | 56 | | |
| Example 10 | PIB rubber adhesive | Db126 (10) | IMQ (3) | WT1$_{35}$ (1) | IPM (25.8) | MA (8.6) | None | micro-cutter | 66 | 29 | | |
| Comparative example 3 | Acrylic adhesiveA | Db126 (10) | None | None | IPM (26.4) | None | None | None | None | 10 | 2 | |
| Comparative example 4 | Acrylic adhesiveA | Db126 (10) | None | None | IPM (26.4) | MA (8.8) | None | None | None | 10 | 11 | |
| Example 11 | Acrylic adhesiveA | Db126 (10) | IMQ (1) | None | IPM (26.4) | MA (8.8) | None | None | None | 10 | 31 | |
| Example 12 | Acrylic adhesiveA | Db126 (10) | IMQ (1) | PEP (1) | IPM (26.4) | MA (8.8) | None | None | None | 10 | 49 | |
| Example 13 | Acrylic adhesiveA | Db126 (10) | None | WT1$_{35}$ (1) | IPM (26.4) | None | None | None | None | 10 | 20 | |
| Example 14 | Acrylic adhesiveA | Db126 (10) | loxoprofen Na (COX inhibitor) (3) | WT1$_{35}$ (1) | IPM (26.4) | None | None | None | None | 10 | 190 | |
| Example 15 | Acrylic adhesiveB | Db126 (10) | IMQ (1) | PEP (1) | IPM (26.4) | MA (8.8) | None | None | None | 10 | 75 | |
| Example 16 | SIS adhesiveA | Db126 (10) | IMQ (1) | PEP (1) | IPM (13.2) Liquid paraffin (13.2) | MA (8.4) | None | None | None | 10 | 377 | |
| Example 17 | SIS-PIB adhesiveA | Db126 (10) | IMQ (1) | PEP (1) | IPM (13.2) Liquid paraffin (13.2) | MA (8.4) | None | None | None | 10 | 277 | |

TABLE 1-continued

| | Composition | | | | | | TSLP (pg/mg protein) | Physical irritation | TEWL (g/hm²) | Results of immunization (ELISPOT average number of spots) | % Specfic Lysis (In vivo CTL assay) |
|---|---|---|---|---|---|---|---|---|---|---|---|
| | Base (Adhesive) | Antigen peptide | Cellular immunity induction promoter | Skin permeability enhancer | Acid | Additive (chemical irritation) | | | | | |
| Example 18 | SIS-PIB adhesive A | Db126 (10) | loxoprofen Na (COX inhibitor) (3) | WT1₃₅ (1) | IPM (13.2) Liquid paraffin (13.2) | None | None | None | 10 | 201 | |
| Example 19 | PIB rubber adhesive | Db126 (10) | IMQ (3) | PEP (1) | IPM (33.0) | octanoic acid (1.7) | None | None | 10 | 25 | |
| Example 20 | PIB rubber adhesive | Db126 (10) | IMQ (3) | PEP (1) | IPM (33.0) | isostearic acid (1.7) | None | None | 10 | 146 | |
| Example 21 | PIB rubber adhesive | Db126 (10) | IMQ (3) | PEP (1) | IPM (25.8) | decanoic acid (8.6) | None | None | 10 | 375 | |
| Example 22 | PIB rubber adhesive | Db126 (10) | IMQ (3) | PEP (1) | IPM (25.8) | lauric acid (8.6) | None | None | 10 | 446 | |
| Example 23 | PIB rubber adhesive | Db126 (10) | IMQ (3) | PEP (1) | IPM (25.8) | palmitic acid (8.6) | None | None | 10 | 40 | |
| Example 24 | PIB rubber adhesive | Db126 (10) | IMQ (3) | PEP (1) | IPM (25.8) | isostearic acid (8.6) | None | None | 10 | 494 | |
| Example 25 | PIB rubber adhesive | Db126 (10) | IMQ (3) | PEP (1) | IPM (25.8) | oleic acid (8.6) | None | None | 10 | 495 | |
| Example 26 | PIB rubber adhesive | Db126 (10) | IMQ (3) | PEP (1) | IPM (25.8) | stearic acid (8.6) | None | None | 10 | 24 | |
| Example 27 | PIB rubber adhesive | Db126 (10) | IMQ (3) | PEP (1) | IPM (31.4) | lactic acid (3) | None | None | 12 | 501 | |
| Example 28 | PIB rubber adhesive | Db126 (10) | c-di-GMP (0.3) | PEP (1) | IPM (25.8) | MA (8.6) | None | None | | 450 | |
| Example 29 | PIB rubber adhesive | Db126 (10) | c-di-AMP (0.3) | PEP (1) | IPM (25.8) | MA (8.6) | None | None | | | |
| Example 30 | PIB rubber adhesive | Db126 (10) | lipopoly-saccharide derived from Pantoea bacterium (TLR 4 ligand) (3) | PEP (1) | IPM (25.8) | MA (8.6) | None | None | 12 | 103 | |
| Example 31 | PIB rubber adhesive | Db126 (10) | glucopyranosyl lipid (TLR4 ligand) (3) | PEP (1) | IPM (25.8) | MA (8.6) | None | None | | | |
| Example 32 | PIB rubber adhesive | Db126 (10) | sodium hyaluronate (TLR4 ligand) (3) | PEP (1) | IPM (25.8) | MA (8.6) | None | None | | | |
| Example 33 | PIB rubber adhesive | Db126 (10) | ODN1826 (TLR9 ligand) (3) | PEP (1) | IPM (25.8) | MA (8.6) | None | None | | | |
| Example 34 | PIB rubber adhesive | Db126 (10) | levamisole hydrochloride (immunomodulatory small molecule drug) (3) | PEP (1) | IPM (25.8) | MA (8.6) | None | None | 12 | 45 | |
| Example 35 | PIB rubber adhesive | Db126 (10) | etodolac (COX inhibitor) (3) | PEP (1) | IPM | MA (8.6) | None | None | | | |

TABLE 1-continued

| | | | Composition | | | | TSLP | | | Results of immunization (ELISPOT | % Specfic Lysis |
|---|---|---|---|---|---|---|---|---|---|---|---|
| | Base (Adhesive) | Antigen peptide | Cellular immunity induction promoter | Skin permeability enhancer | Acid | Additive (chemical irritation) | (pg/mg protein) | Physical irritation | TEWL (g/hm²) | average number of spots) | (In vivo CTL assay) |
| Example 36 | PIB rubber adhesive | Db126 (10) | pidotimod (immuno-modulatory small molecule drug) (3) | PEP (1) | IPM (25.8) | MA (8.6) | None | | None | | |
| Example 37 | PIB rubber adhesive | Db126 (10) | Bestatin (immuno-modulatory small molecule drug) (3) | PEP (1) | IPM (25.8) | MA (8.6) | None | | None | | |
| Example 38 | PIB rubber adhesive | Db126 (10) | None | PEP (1) | IPM (25.8) | MA (8.6) | None | | None | 10 | 41 |
| Example 39 | PIB rubber adhesive | Db126 (10) | loxoprofen Na (COX inhibitor) (3) | PEP (1) | IPM (25.8) | None | None | | None | 10 | 185 |
| Example 40 | PIB rubber adhesive | Db126 (10) | loxoprofen Na (COX inhibitor) (3) | PEP (1) | IPM (25.8) | MA (8.6) | None | | None | 10 | 610 |
| Example 41 | PIB rubber adhesive | Db126 (10) | loxoprofen Na (COX inhibitor) (1.5), IMQ (1.5) | PEP (1) | IPM (25.8) | MA (8.6) | None | | None | 12 | 736 |
| Example 42 | PIB rubber adhesive | Db126 (10) | quercetin (TSLP production inhibitor) (3) | PEP (1) | IPM (25.8) | MA (8.6) | None | | None | 10 | 560 |
| Example 43 | PIB rubber adhesive | Db126 (10) | quercetin (TSLP production inhibitor) (1.5), IMQ (1.5) | PEP (1) | IPM (25.8) | MA (8.6) | None | | None | 12 | 621 |
| Example 44 | PIB rubber adhesive | Db126 (10) | GW627368X (prostaglandin receptor antagonist) (3) | PEP (1) | IPM (25.8) | MA (8.6) | None | | None | 12 | 574 |
| Example 45 | PIB rubber adhesive | Db126 (10) | sulprostone (prostaglandin receptor agonist) (3) | PEP (1) | IPM (25.8) | MA (8.6) | None | | None | 12 | 530 |
| Example 46 | PIB rubber adhesive | Db126 (10) | clofibrate (PPAR agonist) (3) | PEP (1) | IPM (25.8) | MA (8.6) | None | | None | 12 | 610 |
| Example 47 | PIB rubber adhesive | Db126 (10) | tranilast (TGF-beta production inhibitor) (3) | PEP (1) | IPM (25.8) | MA (8.6) | None | | None | 12 | 123 |
| Example 48 | PIB rubber adhesive | Db126 (10) | Immepip (histamine receptor agonist) (3) | PEP (1) | IPM (25.8) | MA (8.6) | None | | None | 12 | 155 |
| Example 49 | PIB rubber adhesive | Db126 (10) | azelastine (histamine receptor antagonist) (3) | PEP (1) | IPM (25.8) | MA (8.6) | None | | None | 12 | 770 |
| Example 50 | PIB rubber adhesive | Db126 (10) | sumatriptan (serotonin receptor agonist) (3) | PEP (1) | IPM (25.8) | MA (8.6) | None | | None | 12 | 790 |

TABLE 1-continued

| | Composition | | | | | | TSLP (pg/mg protein) | Physical irritation | TEWL (g/hm²) | Results of immunization (ELISPOT average number of spots) | % Specific Lysis (In vivo CTL assay) |
|---|---|---|---|---|---|---|---|---|---|---|---|
| | Base (Adhesive) | Antigen peptide | Cellular immunity induction promoter | Skin permeability enhancer | Acid | Additive (chemical irritation) | | | | | |
| Example 51 | PIB rubber adhesive | Db126 (10) | yohimbine (serotonin receotor antagonist) (3) | PEP (1) | IPM (25.8) | MA (8.6) | None | None | 12 | 173 | |
| Example 52 | PIB rubber adhesive | Db126 (10) | oxybutynin (muscarine receptor antagonist) (3) | PEP (1) | IPM (25.8) | MA (8.6) | None | None | 12 | 185 | |
| Example 53 | PIB rubber adhesive | Db126 (10) | tamsulosin (adrenalin receptor antagonist) (3) | PEP (1) | IPM (25.8) | MA (8.6) | None | None | 12 | 171 | |
| Example 54 | PIB rubber adhesive | Db126 (10) | loperamide (opioid receptor agonist) (3) | PEP (1) | IPM (25.8) | MA (8.6) | None | None | 12 | 480 | |
| Example 55 | PIB rubber adhesive | Db126 (10) | melatonin (melatonin receptor agonist) (3) | PEP (1) | IPM (25.8) | MA (8.6) | None | None | 12 | 535 | |
| Example 56 | PIB rubber adhesive | Db126 (10) | L-AP4 (metabotropic glutamate receptor agonist) (3) | PEP (1) | IPM (25.8) | MA (8.6) | None | None | 12 | 111 | |
| Example 57 | PIB rubber adhesive | Db126 (10) | IMQ (3) | PADRE (1) | IPM (25.8) | MA (8.6) | None | None | 12 | 613 | |
| Example 58 | PIB rubber adhesive | Db126 (10) | IMQ (3) | WT1$_{332}$ (1) | IPM (25.8) | MA (8.6) | None | None | 12 | | |
| Example 59 | PIB rubber adhesive | Db126 (10) | IMQ (3) | PEP (1) | IPM) (25.8 | MA (8.6) | None | None | 12 | 560 | |
| Example 60 | PIB rubber adhesive | Db126 (10) | IMQ (3) | PEP (1) | None | MA (8.6) | None | None | 12 | 54 | |

IMQ: Imiquimod (TLR7 and/or TLR8 ligand)
c-di-GMP: Cyclic di-GMP (cyclic dinucleotide)
c-di-AMP: Cyclic di-AMP (cyclic dinucleotide)
PEP: Peptide-25 (SEQ ID NO: 5) (helper peptide)
PADRE: Universal helper peptide (SEQ ID NO: 7) (helper peptide)
WT1$_{35}$: hWT1$_{35}$ helper peptide (SEQ ID NO: 6) (helper peptide)
WT1$_{332}$: WT1$_{332-347}$ helper peptide (SEQ ID NO: 8) (helper peptide)
IPM: Isopropyl myristate, manufactured by Croda Japan K.K.
IPP: Isopropyl palmitate, manufactured by Wako Pure Chemical Industries, Ltd.
MA: Myristic acid
BL-4.2: Polyoxyethylene (4,2) lauryl ether, manufactured by Nikko Chemicals Co., Ltd.
T/S10: Tape stripping 10 times
Db126 peptide is in the form of acetate in all cases.
Values in the parentheses indicate the mixing proportions (parts by weight) of the respective components.

TABLE 2

| No. | Skin treatment | Amount of Db126 peptide permeation (μg/cm²/24 hr) | Amount of imiquimod permeation (μg/cm²/24 hr) |
|---|---|---|---|
| Example 8 | None | 40 | 6.5 |
| Example 10 | Microcutter | 79 | 8.5 |

TABLE 3

| No. | Features | Amount of Db126 peptide permeation (μg/cm²/24 hr) | Amount of imiquimod permeation (μg/cm²/24 hr) |
|---|---|---|---|
| Example 5 | Tape without surfactant | 2.8 | 4.5 |
| Example 6 | BL-4.2-incorporated tape | 13.4 | 5.8 |

Injectable Formulation

Intradermal injectable formulations having the ingredients shown in the following Table 4 were prepared. Specifically, saline as the base was added to Db126 peptide and Montanide ISA51VG (Freund Corporation) as an adjuvant at the amounts described in Table 4, to the total of 100 parts by weight, and the mixture was kneaded with a homogenizer to prepare emulsion-like injectable formulation.

Mouse Immunization Test 2 (Injectable)

Using an injectable produced as described above, mouse immunization test was performed in the same manner as in the mouse immunization test 1. 30 µL of the injectable formulation was administered once to the back of mouse by intradermal injection and the spleen was isolated 6 days after the administration. Genetically modified mouse which can be used to evaluate the cellular immunity inducing ability of the HLA-A*0201 type MHC restricted peptide was used as model animal. The results of the immunization test are shown in the following Table 4.

In the comparative Examples 3 to 7, the amount of the injected Db126 peptide was calculated as the intradermal introduction amount because the peptide was injected intradermally. In addition, mouse skin permeability test was performed with the preparation of Example 7, the amount of the peptide permeated into the skin for 24 hours was compared with the intradermally introduced amount of the peptide. The comparison of the intradermal introduction amount between injection and the tape preparation is shown in Table 5.

is shown that cellular immune response cannot be enhanced even when the skin permeated amount is increased.

Figure 3:
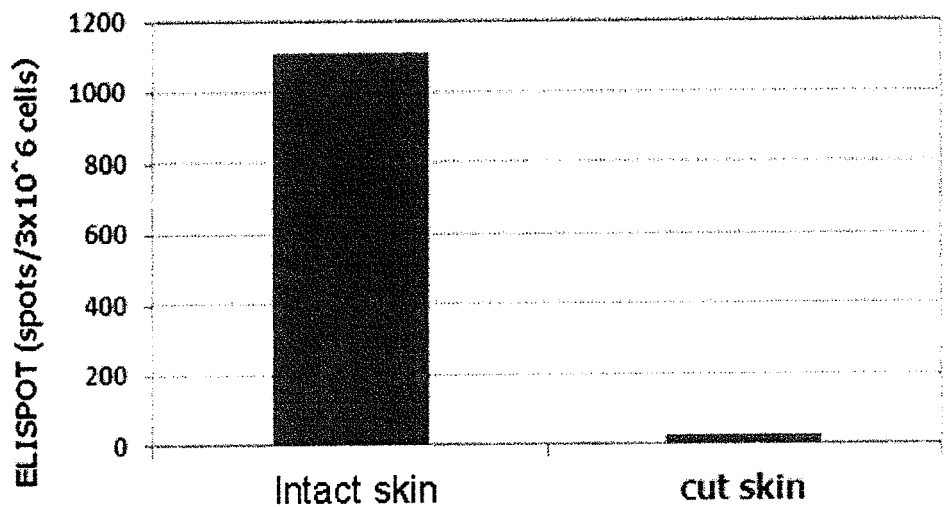
FIG. 3 shows the comparison of immunity when a tape preparation is applied to a normal skin or a physically-damaged skin.

The results of the mouse immunization test and the mouse skin permeability test of Examples 8 and 10 in which influence of physical irritation was studied are shown in FIG. 3 and Table 2. When the tape preparation was applied to the skin to which physical irritation had been given, the immunity induction level was attenuated, and it is shown that administration under the mildly irritating condition is effective. Meanwhile, in Table 2, the skin permeated amounts of Db126 and imiquimod were increased by physical irritation, and thus, it is shown that cellular immune response cannot be enhanced even when the skin permeated amount is increased.

Figure 4:
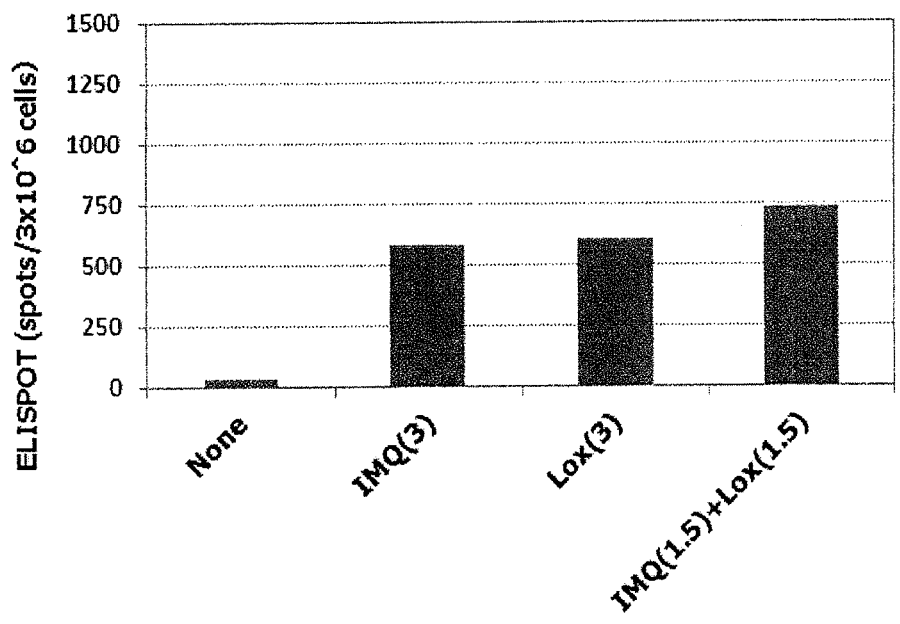
FIG. 4 is a diagram illustrating a synergistic effect of imiquimod and loxoprofen Na.
Figure 5:
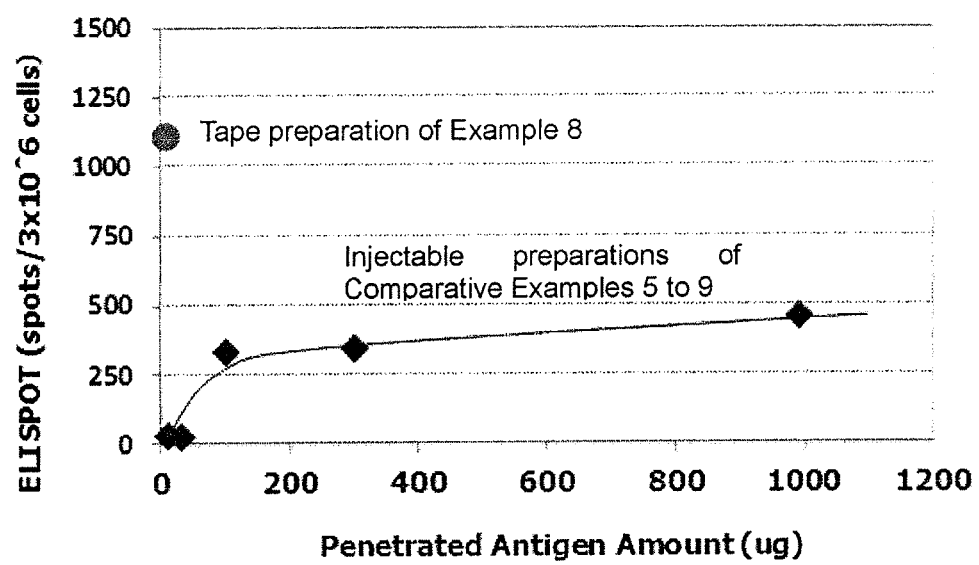
FIG. 5 is a diagram illustrating a comparison of immunity induction between cancer vaccine tape preparations of the present invention (containing imiquimod, hWT1$_{35}$ and myristic acid) and an injection.

The results of the mouse immunization test of Examples 38, 7, 40 and 41 in which the synergistic effect of imiquimod and loxoprofen Na was studied are shown in FIG. 4. It is shown that the immunity induction level is higher when both of imiquimod (1.5%) and loxoprofen Na (1.5%) are added, than when imiquimod alone (3%) or loxoprofen Na alone (3%) is administered.

In Table 1, cellular immunity induction promoters were evaluated in regard to vaccine tape preparation comprising WT1 peptide and/or modified WT1 peptide. It was found that a first cellular immunity induction promoter selected from TLR ligand, cyclic dinucleotide, helper peptide, immunomodulatory small molecule drug, cyclooxygenase inhibitor, TSLP production inhibitor, prostaglandin receptor antagonist, prostaglandin receptor agonist, PPAR agonist,

TABLE 4

| | Base | Antigen peptide | Cellular immunity induction promoter | Results of immunization (ELISPOT average number of spots) | % Specific Lysis (In vivo CTL assay) |
|---|---|---|---|---|---|
| Comparative Example 5 | Physiological saline | Db126 (0.033) | Montanide ISA51VG (50) | 33 | |
| Comparative Example 6 | Physiological saline | Db126 (0.1) | Montanide ISA51VG (50) | 28 | |
| Comparative Example 7 | Physiological saline | Db126 (0.33) | Montanide ISA51VG (50) | 335 | |
| Comparative Example 8 | Physiological saline | Db126 (1) | Montanide ISA51VG (50) | 347 | |
| Comparative Example 9 | Physiological saline | Db126 (3.3) | Montanide ISA51VG (50) | 461 | 32 |

Db126 peptide is in the form of acetate (salt) in all cases.
A numerical value in parenthesis is the blending ratio (part(s) by weight) of each ingredient.

TABLE 5

| No. | Amount of Db126 peptide introduced into skin (µg) |
|---|---|
| Example 8 | 7 |
| Comparative Example 5 | 9.9 |
| Comparative Example 6 | 30 |
| Comparative Example 7 | 99 |
| Comparative Example 8 | 300 |
| Comparative Example 9 | 990 |

Figure 2:
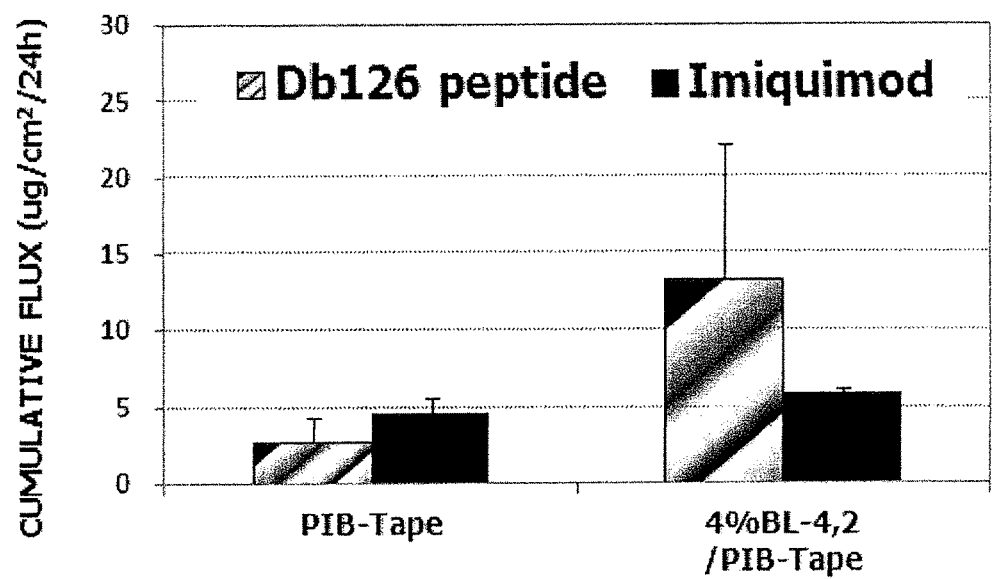
FIG. 2 is a diagram illustrating a comparison of skin permeability between a tape preparation containing no surfactant and a tape preparation containing a surfactant.

The results of the mouse immunization test and the mouse skin permeability test of Examples 5 and 6 in which influence of chemical irritation (surfactant) was studied are shown in FIG. 1 and FIG. 2. From FIG. 1, it is shown that cellular immune response is attenuated by chemical irritation, and administration under the mildly irritating condition is effective. In FIG. 2, the skin permeated amounts of Db126 and imiquimod were increased by chemical irritation, and it TGF-beta production inhibitor, histamine receptor agonist, histamine receptor antagonist, serotonin receptor agonist, serotonin receptor antagonist, muscarine receptor antagonist, adrenalin receptor antagonist, opioid receptor agonist, melatonin receptor agonist, metabotropic glutamate receptor agonist and a combination of two or more kinds of them was effective.

Preferably, a first cellular immunity induction promoter selected from TLR ligand, cyclic dinucleotide, cyclooxygenase inhibitor, TSLP production inhibitor, prostaglandin receptor antagonist, prostaglandin receptor agonist, PPAR agonist, TGF-beta production inhibitor, histamine receptor agonist, histamine receptor antagonist, serotonin receptor agonist, serotonin receptor antagonist, muscarine receptor antagonist, adrenalin receptor antagonist, opioid receptor agonist, melatonin receptor agonist, metabotropic glutamate receptor agonist and a combination of two or more kinds of them, as well as a combination of helper peptide with the first cellular immunity induction promoter other than helper peptide were effective.

More preferably, a first cellular immunity induction promoter selected from TLR7 and/or TLR8 ligand, cyclic dinucleotide, cyclooxygenase inhibitor, TSLP production inhibitor, prostaglandin receptor antagonist, prostaglandin receptor agonist, PPAR agonist, histamine receptor antagonist, serotonin receptor agonist, opioid receptor agonist, melatonin receptor agonist and a combination of two or more kinds of them, as well as a combination of helper peptide with the first cellular immunity induction promoter other than helper peptide were particularly effective.

It was also found that cellular immunity induction was promoted by an addition of a pharmacologically acceptable acid or a pharmacologically acceptable salt thereof as a second cellular immunity induction promoter. Specifically, octanoic acid, isostearic acid, decanoic acid, lauric acid, palmitic acid, stearic acid, myristic acid, oleic acid, and lactic acid were effective.

Preferably, decanoic acid, lauric acid, myristic acid, isostearic acid, oleic acid, and lactic acid were effective.

More preferably, lauric acid, myristic acid, isostearic acid, oleic acid, and lactic acid were particularly effective.

As shown in Table 1 and Table 4, the transdermal administration of the cancer vaccine tape preparation comprising the WT1 peptide and/or modified WT1 peptide can induce cellular immune response equivalent to or stronger than the immune response induced by injecting the antigen. Current Opinion in Immunology 2008, 20:211-220 reported results of clinical studies and confirmed that the WT1 vaccine was useful as cancer vaccine when administered by injection. The application of the vaccine tape preparation of the present invention to the skin could induce cellular immune response that is equivalent to or stronger than the immune response induced by injection in mice, and therefore, it is expected that the tape preparation of the present invention can also effectively induce cellular immune response that is comparative to or stronger than the immune response induced by injection. The vaccine tape preparation is a useful cancer vaccine.

As shown in Table 2, the skin permeated amounts of Db126 and imiquimod were increased by a pretreatment (physical stimuli) to the skin. However, as indicated in Table 1, cellular immunity was rather attenuated. From these results, it is understood that it is important to administer the antigen and the adjuvant under mildly irritating conditions, rather than to increase the skin permeated amounts of the antigen and the adjuvant.

What is claimed is:

1. A method for inducing cellular immunity in a subject, which comprises applying a cancer vaccine tape preparation, comprising:
 a support, and
 an adhesive layer comprising an adhesive disposed on one side of the support, wherein the adhesive layer carries a combination of:
  (i) a WT1 peptide and/or a modified WT1 peptide;
  (ii) imiquimod;
  (iii) at least one helper peptide and/or modified helper peptide; and
  (iv) myristic acid,
 to the skin of the subject under a mildly irritating condition.

2. The method according to claim 1, wherein the method is for treating a cancer in the subject.

3. The method according to claim 1, wherein the adhesive of the tape preparation is an acrylic adhesive.

4. The method according to claim 1, wherein the adhesive of the tape preparation is a rubber-based adhesive.

5. The method according to claim 4, wherein the rubber-based adhesive is polyisobutylene rubber adhesive.

6. The method according to claim 1, wherein the adhesive of the tape preparation is a silicone-based adhesive.

7. The method according to claim 1, wherein the adhesive layer further carries a skin permeability enhancer.

8. The method according to claim 1, wherein the mildly irritating condition is a condition under which transepidermal water loss (TEWL) in a model animal for skin irritation evaluation before the administration of the composition is 50 g/h·m² or less.

9. The method according to claim 1, wherein the mildly irritating condition is a condition under which the cutaneous TSLP level in a model animal for skin irritation evaluation at completion of the administration of the composition is 10000 pg/mg protein or less.

10. The method according to claim 1, wherein the helper peptide is at least tubercle bacillus-derived helper peptide, measles virus-derived helper peptide, hepatitis B virus-derived helper peptide, hepatitis C virus-derived helper peptide, *Chlamydia trachomatis*-derived helper peptide, *Plasmodium falciparum* sporozoite-derived helper peptide, keyhole limpet haemocyanin-derived helper peptide, tetanus toxin-derived helper peptide, universal helper analog or cancer cell-derived helper peptide, excepting a WT1-derived helper peptide.

11. The method according to claim 1, wherein the cancer vaccine tape preparation also comprises a cyclooxygenase inhibitor.

12. The method according to claim 1, wherein the helper peptide is hWT1$_{35}$ helper peptide, hWT1$_{86}$ helper peptide, or hWT1$_{294}$ helper peptide.

13. A cancer vaccine tape preparation for use in the induction of cellular immunity, comprising:
 a support, and
 an adhesive layer comprising an adhesive disposed on one side of the support, wherein the adhesive layer carries a combination of:
  (i) a WT1 peptide and/or a modified WT1 peptide;
  (ii) imiquimod;
  (iii) at least one helper peptide and/or modified helper peptide; and
  (iv) myristic acid,
 wherein the tape preparation is structurally configured and arranged for application to the skin of a subject.

14. The cancer vaccine tape preparation for use in the induction of cellular immunity according to claim 13, wherein the helper peptide is at least tubercle bacillus-derived helper peptide, measles virus-derived helper peptide, hepatitis B virus-derived helper peptide, hepatitis C virus-derived helper peptide, *Chlamydia trachomatis*-derived helper peptide, *Plasmodium falciparum* sporozoite-derived helper peptide, keyhole limpet haemocyanin-derived helper peptide, tetanus toxin-derived helper peptide, universal helper analog or cancer cell-derived helper peptide, excepting a WT1-derived helper peptide.

15. The cancer vaccine tape preparation for use in the induction of cellular immunity according to claim 13, wherein the adhesive layer also carries a cyclooxygenase inhibitor.

* * * * *

SEQUENCE LISTING

```
<160> NUMBER OF SEQ ID NOS: 10

<210> SEQ ID NO 1
<211> LENGTH: 9
<212> TYPE: PRT
<213> ORGANISM: Homo sapiens

<400> SEQUENCE: 1

Arg Met Phe Pro Asn Ala Pro Tyr Leu
1               5

<210> SEQ ID NO 2
<211> LENGTH: 9
<212> TYPE: PRT
<213> ORGANISM: Homo sapiens

<400> SEQUENCE: 2

Cys Met Thr Trp Asn Gln Met Asn Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Tyr Thr Trp Asn Gln Met Asn Leu
1               5

<210> SEQ ID NO 4
<211> LENGTH: 20
<212> TYPE: DNA
<213> ORGANISM: Unknown
<220> FEATURE:
<223> OTHER INFORMATION: Description of Unknown: Bacterial DNA
      sequence

<400> SEQUENCE: 4
```
tccatgacgt tcctgacgtt                           20

<210> SEQ ID NO 5
<211> LENGTH: 15
<212> TYPE: PRT
<213> ORGANISM: Mycobacterium tuberculosis

<400> SEQUENCE: 5

Phe Gln Asp Ala Tyr Asn Ala Ala Gly Gly His Asn Ala Val Phe
1               5                   10                  15

<210> SEQ ID NO 6
<211> LENGTH: 18
<212> TYPE: PRT
<213> ORGANISM: Homo sapiens

<400> SEQUENCE: 6

Trp Ala Pro Val Leu Asp Phe Ala Pro Pro Gly Ala Ser Ala Tyr Gly
1               5                   10                  15

Ser Leu

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (3)..(3)
<223> OTHER INFORMATION: Cyclohexylalanine
<220> FEATURE:
<221> NAME/KEY: MOD_RES
<222> LOCATION: (13)..(13)
<223> OTHER INFORMATION: D-Ala

<400> SEQUENCE: 7

Ala Lys Ala Val Ala Ala Trp Thr Leu Lys Ala Ala Ala
1               5                   10

<210> SEQ ID NO 8
<211> LENGTH: 16
<212> TYPE: PRT
<213> ORGANISM: Homo sapiens

<400> SEQUENCE: 8

Lys Arg Tyr Phe Lys Leu Ser His Leu Gln Met His Ser Arg Lys His
1               5                   10                  15

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Lys Lys Lys Lys
1               5

<210> SEQ ID NO 10

-continued

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Asp Pro Lys His Pro Lys Ser Phe
1               5
```